(12) United States Patent
Stone et al.

(10) Patent No.: US 8,562,645 B2
(45) Date of Patent: Oct. 22, 2013

(54) METHOD AND APPARATUS FOR FORMING A SELF-LOCKING ADJUSTABLE LOOP

(75) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/098,897

(22) Filed: May 2, 2011

(65) Prior Publication Data

US 2011/0208239 A1    Aug. 25, 2011

Related U.S. Application Data

(63) Continuation-in-part of application No. 12/702,067, filed on Feb. 8, 2010, which is a continuation of application No. 11/541,505, filed on Sep. 29, 2006, now Pat. No. 7,658,751, application No. 13/098,897, which is a continuation-in-part of application No. 12/719,337, filed on Mar. 8, 2010, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 13/098,897, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, application No. 13/098,897, which is a continuation-in-part of application No. 12/196,398, filed on Aug. 22, 2008, now Pat. No. 7,959,650, which is a continuation-in-part of application No. 11/784,821, filed on Apr. 10, 2007.

(51) Int. Cl.
*A61B 17/04* (2006.01)
*A61L 17/00* (2006.01)

(52) U.S. Cl.
USPC .......................................... 606/228; 606/232

(58) Field of Classification Search
USPC .......... 623/13.11–13.2; 606/70, 71, 280–299, 606/74, 228, 232, 233, 213, 151; 600/37, 600/29, 30
See application file for complete search history.

(56) References Cited

U.S. PATENT DOCUMENTS

| | | |
|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A * | 11/1885 | Binns .......................... 474/253 |
| 401,677 A | 4/1889 | Autenrieth |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |

| Patent No. | Date | Name |
|---|---|---|
| 2,528,456 A | 10/1950 | Stevenson |
| 2,562,419 A | 7/1951 | Ferris |
| 2,581,564 A | 1/1952 | Villegas |
| 2,600,395 A * | 6/1952 | Domoj et al. ..................... 87/13 |
| 2,610,631 A | 9/1952 | Calicchio |
| 2,665,597 A | 1/1954 | Hill |
| 2,669,774 A | 2/1954 | Mitchell |
| 2,698,986 A * | 1/1955 | Brown ........................ 289/1.2 |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A * | 7/1977 | Burnett ............................ 87/8 |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A * | 7/1978 | McGrew ...................... 289/1.5 |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |

| | | | | | | |
|---|---|---|---|---|---|---|
| 4,462,395 A | 7/1984 | Johnson | | 4,793,363 A | 12/1988 | Ausherman et al. |
| 4,463,753 A | 8/1984 | Gustilo | | 4,809,695 A | 3/1989 | Gwathmey et al. |
| 4,473,102 A | 9/1984 | Ohman et al. | | 4,813,406 A | 3/1989 | Ogle, II |
| 4,484,570 A | 11/1984 | Sutter et al. | | 4,823,794 A | 4/1989 | Pierce |
| 4,489,446 A | 12/1984 | Reed | | 4,828,562 A | 5/1989 | Kenna |
| 4,493,323 A | 1/1985 | Albright et al. | | 4,832,026 A | 5/1989 | Jones |
| 4,496,468 A | 1/1985 | House et al. | | 4,834,098 A | 5/1989 | Jones |
| 4,505,274 A | 3/1985 | Speelman | | 4,838,282 A | 6/1989 | Strasser et al. |
| 4,509,516 A | 4/1985 | Richmond | | 4,841,960 A | 6/1989 | Garner |
| 4,531,522 A | 7/1985 | Bedi et al. | | 4,851,005 A | 7/1989 | Hunt et al. |
| 4,532,926 A | 8/1985 | O'Holla | | 4,858,608 A | 8/1989 | McQuilkin et al. |
| 4,534,350 A | 8/1985 | Golden et al. | | 4,860,513 A | 8/1989 | Whitman |
| 4,535,764 A | 8/1985 | Ebert | | 4,863,383 A | 9/1989 | Grafelmann et al. |
| 4,537,185 A | 8/1985 | Stednitz | | 4,870,957 A | 10/1989 | Goble et al. |
| 4,549,545 A | 10/1985 | Levy | | 4,873,976 A | 10/1989 | Schreiber |
| 4,549,652 A | 10/1985 | Free | | 4,887,601 A | 12/1989 | Richards |
| 4,561,432 A | 12/1985 | Mazor | | 4,890,615 A | 1/1990 | Caspari et al. |
| 4,564,007 A | 1/1986 | Coombs et al. | | 4,893,619 A | 1/1990 | Dale et al. |
| 4,570,623 A | 2/1986 | Ellison et al. | | 4,893,974 A | 1/1990 | Fischer et al. |
| 4,573,844 A | 3/1986 | Smith | | 4,895,148 A | 1/1990 | Bays et al. |
| 4,576,608 A | 3/1986 | Homsy | | 4,896,668 A | 1/1990 | Popoff et al. |
| 4,584,722 A | 4/1986 | Levy et al. | | 4,898,156 A | 2/1990 | Gatturna et al. |
| 4,590,928 A | 5/1986 | Hunt et al. | | 4,899,743 A | 2/1990 | Nicholson et al. |
| 4,595,007 A | 6/1986 | Mericle | | 4,901,721 A | 2/1990 | Hakki |
| 4,596,249 A | 6/1986 | Freda et al. | | 4,922,897 A | 5/1990 | Sapega et al. |
| 4,602,635 A | 7/1986 | Mulhollan et al. | | 4,923,461 A | 5/1990 | Caspari et al. |
| 4,602,636 A | 7/1986 | Noiles | | 4,927,421 A | 5/1990 | Goble et al. |
| 4,604,997 A | 8/1986 | De Bastiani et al. | | 4,946,377 A | 8/1990 | Kovach |
| 4,605,414 A | 8/1986 | Czajka | | 4,946,468 A | 8/1990 | Li |
| 4,616,650 A | 10/1986 | Green et al. | | 4,950,270 A | 8/1990 | Bowman et al. |
| 4,621,640 A | 11/1986 | Mulhollan et al. | | 4,950,285 A | 8/1990 | Wilk |
| 4,624,254 A | 11/1986 | McGarry et al. | | 4,960,381 A | 10/1990 | Niznick |
| 4,632,100 A | 12/1986 | Somers et al. | | 4,961,741 A | 10/1990 | Hayhurst |
| 4,635,637 A | 1/1987 | Schreiber | | 4,968,315 A | 11/1990 | Gatturna |
| 4,636,121 A | 1/1987 | Miller | | 4,968,317 A | 11/1990 | Tormala et al. |
| 4,641,652 A | 2/1987 | Hutterer et al. | | 4,969,886 A | 11/1990 | Cziffer et al. |
| 4,649,916 A | 3/1987 | Frimberger | | 4,974,488 A * | 12/1990 | Spralja .............................. 87/8 |
| 4,649,952 A | 3/1987 | Jobe | | 4,976,736 A | 12/1990 | White et al. |
| 4,653,486 A | 3/1987 | Coker | | 4,978,350 A | 12/1990 | Wagenknecht et al. |
| 4,653,487 A | 3/1987 | Maale | | 4,979,956 A | 12/1990 | Silvestrini |
| 4,653,489 A | 3/1987 | Tronzo | | 4,983,176 A | 1/1991 | Cushman et al. |
| 4,655,777 A | 4/1987 | Dunn et al. | | 4,988,351 A | 1/1991 | Paulos et al. |
| 4,662,068 A | 5/1987 | Polonsky | | 4,994,074 A | 2/1991 | Bezwada et al. |
| 4,667,662 A | 5/1987 | Titone et al. | | 4,997,433 A | 3/1991 | Goble et al. |
| 4,667,675 A | 5/1987 | Davis | | 5,002,550 A | 3/1991 | Li |
| 4,669,473 A | 6/1987 | Richards et al. | | 5,002,562 A | 3/1991 | Oberlander |
| 4,683,895 A | 8/1987 | Pohndorf | | 5,002,574 A | 3/1991 | May et al. |
| 4,688,561 A | 8/1987 | Reese | | 5,007,921 A | 4/1991 | Brown |
| 4,690,169 A | 9/1987 | Jobe | | 5,030,224 A | 7/1991 | Wright et al. |
| 4,696,300 A | 9/1987 | Anderson | | 5,030,235 A | 7/1991 | Campbell, Jr. |
| 4,705,040 A | 11/1987 | Mueller et al. | | 5,035,701 A | 7/1991 | Kabbara |
| 4,708,132 A | 11/1987 | Silvestrini | | 5,037,422 A | 8/1991 | Hayhurst et al. |
| 4,714,475 A | 12/1987 | Grundei et al. | | 5,037,426 A | 8/1991 | Goble et al. |
| 4,716,893 A | 1/1988 | Fischer et al. | | 5,041,129 A | 8/1991 | Hayhurst et al. |
| 4,719,671 A | 1/1988 | Ito et al. | | 5,046,513 A | 9/1991 | Gatturna et al. |
| 4,719,917 A | 1/1988 | Barrows et al. | | 5,047,030 A | 9/1991 | Draenert et al. |
| 4,723,540 A | 2/1988 | Gilmer, Jr. | | 5,053,046 A | 10/1991 | Janese |
| 4,724,839 A | 2/1988 | Bedi et al. | | 5,053,047 A | 10/1991 | Yoon |
| 4,728,332 A | 3/1988 | Albrektsson | | 5,059,201 A | 10/1991 | Asnis |
| 4,738,255 A | 4/1988 | Goble et al. | | 5,059,206 A | 10/1991 | Winters |
| 4,739,751 A | 4/1988 | Sapega et al. | | 5,061,277 A | 10/1991 | Carpentier et al. |
| 4,741,330 A | 5/1988 | Hayhurst | | 5,062,344 A * | 11/1991 | Gerker ................................ 87/8 |
| 4,741,336 A | 5/1988 | Failla et al. | | 5,062,843 A | 11/1991 | Mahony, III |
| 4,744,353 A | 5/1988 | McFarland | | 5,064,431 A | 11/1991 | Gilbertson et al. |
| 4,744,793 A | 5/1988 | Parr et al. | | 5,071,420 A | 12/1991 | Paulos et al. |
| 4,750,492 A | 6/1988 | Jacobs | | 5,074,874 A | 12/1991 | Yoon et al. |
| 4,760,843 A | 8/1988 | Fischer et al. | | 5,078,731 A | 1/1992 | Hayhurst |
| 4,760,844 A | 8/1988 | Kyle | | 5,078,843 A | 1/1992 | Pratt |
| 4,760,848 A | 8/1988 | Hasson | | 5,084,050 A | 1/1992 | Draenert |
| 4,770,663 A | 9/1988 | Hanslik et al. | | 5,084,058 A | 1/1992 | Li |
| 4,772,261 A | 9/1988 | Von Hoff et al. | | 5,085,661 A | 2/1992 | Moss |
| 4,772,286 A | 9/1988 | Goble et al. | | 5,087,263 A | 2/1992 | Li |
| 4,773,910 A | 9/1988 | Chen et al. | | 5,087,309 A * | 2/1992 | Melton, Jr. .................... 156/198 |
| 4,775,380 A | 10/1988 | Seedhom et al. | | 5,089,012 A | 2/1992 | Prou |
| 4,776,328 A | 10/1988 | Frey et al. | | 5,092,866 A | 3/1992 | Breard et al. |
| 4,781,190 A | 11/1988 | Lee et al. | | 5,098,435 A | 3/1992 | Stednitz et al. |
| 4,784,126 A | 11/1988 | Hourahane et al. | | 5,100,415 A | 3/1992 | Hayhurst |
| 4,787,882 A | 11/1988 | Claren et al. | | 5,100,417 A | 3/1992 | Cerier et al. |
| 4,790,297 A | 12/1988 | Luque et al. | | 5,108,433 A | 4/1992 | May et al. |

| | | | | | | |
|---|---|---|---|---|---|---|
| 5,116,337 A | 5/1992 | Johnson | | 5,333,625 A | 8/1994 | Klein |
| 5,116,373 A | 5/1992 | Jakob et al. | | 5,334,204 A | 8/1994 | Clewett et al. |
| 5,116,375 A | 5/1992 | Hofmann | | 5,336,229 A | 8/1994 | Noda |
| 5,123,913 A | 6/1992 | Wilk et al. | | 5,336,231 A | 8/1994 | Adair |
| 5,123,914 A | 6/1992 | Cope | | 5,336,240 A | 8/1994 | Metzler et al. |
| 5,127,785 A | 7/1992 | Faucher et al. | | 5,339,870 A | 8/1994 | Green et al. |
| 5,129,901 A | 7/1992 | Decoste | | 5,342,369 A | 8/1994 | Harryman, II |
| 5,129,902 A | 7/1992 | Goble et al. | | 5,346,462 A | 9/1994 | Barber |
| 5,129,904 A | 7/1992 | Illi et al. | | 5,350,380 A | 9/1994 | Goble et al. |
| 5,129,906 A | 7/1992 | Ross et al. | | RE34,762 E | 10/1994 | Goble et al. |
| 5,139,498 A | 8/1992 | Astudillo Ley | | 5,354,298 A | 10/1994 | Lee et al. |
| 5,139,499 A | 8/1992 | Small et al. | | 5,356,412 A | 10/1994 | Golds et al. |
| 5,139,520 A | 8/1992 | Rosenberg | | 5,356,413 A | 10/1994 | Martins et al. |
| 5,143,498 A | 9/1992 | Whitman | | 5,356,417 A | 10/1994 | Golds |
| 5,147,362 A | 9/1992 | Goble | | 5,358,511 A | 10/1994 | Gatturna et al. |
| 5,149,329 A | 9/1992 | Richardson | | 5,360,431 A | 11/1994 | Puno et al. |
| 5,151,104 A | 9/1992 | Kenna | | 5,362,294 A | 11/1994 | Seitzinger |
| 5,152,790 A | 10/1992 | Rosenberg et al. | | 5,364,400 A | 11/1994 | Rego, Jr. et al. |
| 5,154,189 A | 10/1992 | Oberlander | | 5,366,461 A | 11/1994 | Blasnik |
| 5,156,616 A | 10/1992 | Meadows et al. | | 5,368,599 A | 11/1994 | Hirsch et al. |
| 5,163,960 A | 11/1992 | Bonutti | | 5,370,661 A | 12/1994 | Branch |
| D331,626 S | 12/1992 | Hayhurst et al. | | 5,370,662 A | 12/1994 | Stone et al. |
| 5,169,400 A | 12/1992 | Muhling et al. | | 5,372,146 A | 12/1994 | Branch |
| 5,176,682 A | 1/1993 | Chow | | 5,372,604 A | 12/1994 | Trott |
| 5,178,629 A | 1/1993 | Kammerer | | 5,372,821 A | 12/1994 | Badylak et al. |
| 5,183,458 A | 2/1993 | Marx | | 5,374,268 A | 12/1994 | Sander |
| 5,192,282 A | 3/1993 | Draenert et al. | | 5,374,269 A | 12/1994 | Rosenberg |
| 5,197,987 A | 3/1993 | Koch et al. | | 5,379,492 A | 1/1995 | Glesser |
| 5,203,784 A | 4/1993 | Ross et al. | | 5,383,878 A | 1/1995 | Roger et al. |
| 5,203,787 A | 4/1993 | Noblitt et al. | | 5,383,904 A | 1/1995 | Totakura et al. |
| 5,207,679 A | 5/1993 | Li | | 5,385,567 A | 1/1995 | Goble |
| 5,209,753 A | 5/1993 | Biedermann et al. | | 5,391,171 A | 2/1995 | Schmieding |
| 5,209,805 A | 5/1993 | Spraggins | | 5,391,176 A | 2/1995 | de la Torre |
| 5,211,647 A | 5/1993 | Schmieding | | 5,391,182 A | 2/1995 | Chin |
| 5,211,650 A | 5/1993 | Noda | | 5,393,302 A | 2/1995 | Clark et al. |
| 5,214,987 A | 6/1993 | Fenton, Sr. | | RE34,871 E | 3/1995 | McGuire et al. |
| 5,219,359 A | 6/1993 | McQuilkin et al. | | 5,397,356 A | 3/1995 | Goble et al. |
| 5,222,976 A | 6/1993 | Yoon | | 5,403,328 A | 4/1995 | Shallman |
| 5,224,946 A | 7/1993 | Hayhurst et al. | | 5,403,329 A | 4/1995 | Hinchcliffe |
| 5,230,699 A | 7/1993 | Grasinger | | 5,403,348 A | 4/1995 | Bonutti |
| 5,232,436 A | 8/1993 | Janevski | | 5,405,359 A | 4/1995 | Pierce |
| 5,234,435 A | 8/1993 | Seagrave, Jr. | | 5,417,691 A | 5/1995 | Hayhurst |
| 5,235,238 A | 8/1993 | Nomura et al. | | 5,417,698 A | 5/1995 | Green et al. |
| 5,236,445 A | 8/1993 | Hayhurst et al. | | 5,417,712 A | 5/1995 | Whittaker et al. |
| 5,236,461 A | 8/1993 | Forte | | 5,423,819 A | 6/1995 | Small et al. |
| 5,242,447 A | 9/1993 | Borzone | | 5,423,821 A | 6/1995 | Pasque |
| 5,246,441 A | 9/1993 | Ross et al. | | 5,423,823 A | 6/1995 | Schmieding |
| 5,249,899 A | 10/1993 | Wilson | | 5,423,860 A | 6/1995 | Lizardi et al. |
| 5,250,053 A | 10/1993 | Snyder | | 5,425,733 A | 6/1995 | Schmieding |
| 5,258,015 A | 11/1993 | Li et al. | | 5,425,766 A | 6/1995 | Bowald et al. |
| 5,258,016 A | 11/1993 | DiPoto et al. | | 5,433,751 A | 7/1995 | Christel et al. |
| 5,258,040 A | 11/1993 | Bruchman et al. | | 5,437,680 A | 8/1995 | Yoon |
| 5,261,908 A | 11/1993 | Campbell, Jr. | | 5,437,685 A | 8/1995 | Blasnik |
| 5,268,001 A | 12/1993 | Nicholson et al. | | 5,439,684 A | 8/1995 | Prewett et al. |
| 5,269,160 A | 12/1993 | Wood | | 5,441,508 A | 8/1995 | Gazielly et al. |
| 5,269,783 A | 12/1993 | Sander | | 5,443,468 A | 8/1995 | Johnson |
| 5,269,806 A | 12/1993 | Sardelis et al. | | 5,443,482 A | 8/1995 | Stone et al. |
| 5,269,809 A | 12/1993 | Hayhurst et al. | | 5,443,483 A | 8/1995 | Kirsch et al. |
| 5,279,311 A | 1/1994 | Snyder | | 5,443,509 A | 8/1995 | Boucher et al. |
| 5,281,422 A | 1/1994 | Badylak et al. | | 5,445,833 A | 8/1995 | Badylak et al. |
| 5,282,809 A | 2/1994 | Kammerer et al. | | 5,447,512 A | 9/1995 | Wilson et al. |
| 5,282,832 A | 2/1994 | Toso et al. | | 5,449,361 A | 9/1995 | Preissman |
| 5,282,867 A | 2/1994 | Mikhail | | 5,451,203 A | 9/1995 | Lamb |
| 5,285,040 A | 2/1994 | Brandberg et al. | | 5,454,811 A | 10/1995 | Huebner |
| 5,290,217 A | 3/1994 | Campos | | 5,454,821 A | 10/1995 | Harm et al. |
| 5,306,301 A | 4/1994 | Graf et al. | | 5,456,685 A | 10/1995 | Huebner |
| 5,312,410 A | 5/1994 | Miller et al. | | 5,456,722 A | 10/1995 | McLeod et al. |
| 5,312,422 A | 5/1994 | Trott | | 5,458,601 A | 10/1995 | Young, Jr. et al. |
| 5,312,438 A | 5/1994 | Johnson | | 5,458,604 A | 10/1995 | Schmieding |
| 5,314,429 A | 5/1994 | Goble | | 5,462,542 A | 10/1995 | Alesi, Jr. |
| 5,318,566 A | 6/1994 | Miller | | 5,462,560 A | 10/1995 | Stevens |
| 5,318,575 A | 6/1994 | Chesterfield et al. | | 5,464,426 A | 11/1995 | Bonutti |
| 5,318,577 A | 6/1994 | Li | | 5,464,427 A | 11/1995 | Curtis et al. |
| 5,318,578 A | 6/1994 | Hasson | | 5,464,440 A | 11/1995 | Johansson et al. |
| 5,320,115 A | 6/1994 | Kenna | | 5,466,237 A | 11/1995 | Byrd, III et al. |
| 5,320,626 A | 6/1994 | Schmieding | | 5,467,786 A | 11/1995 | Allen et al. |
| 5,320,633 A | 6/1994 | Allen et al. | | 5,470,334 A | 11/1995 | Ross et al. |
| 5,324,308 A | 6/1994 | Pierce | | 5,470,337 A | 11/1995 | Moss |
| 5,330,489 A | 7/1994 | Green et al. | | 5,470,338 A | 11/1995 | Whitfield et al. |

| | | | | | | |
|---|---|---|---|---|---|---|
| 5,472,452 A | 12/1995 | Trott | | 5,613,971 A | 3/1997 | Lower et al. |
| 5,474,565 A | 12/1995 | Trott | | 5,618,290 A | 4/1997 | Toy et al. |
| 5,474,568 A | 12/1995 | Scott | | 5,626,611 A | 5/1997 | Liu et al. |
| 5,474,572 A | 12/1995 | Hayhurst | | 5,626,614 A | 5/1997 | Hart |
| 5,478,344 A | 12/1995 | Stone et al. | | 5,628,756 A * | 5/1997 | Barker et al. .................. 606/139 |
| 5,478,345 A | 12/1995 | Stone et al. | | 5,628,766 A | 5/1997 | Johnson |
| 5,480,403 A | 1/1996 | Lee et al. | | 5,630,824 A | 5/1997 | Hart |
| 5,480,406 A | 1/1996 | Nolan et al. | | 5,632,748 A | 5/1997 | Beck, Jr. et al. |
| 5,484,442 A | 1/1996 | Melker et al. | | 5,641,256 A | 6/1997 | Gundy |
| 5,486,197 A | 1/1996 | Le et al. | | 5,643,266 A | 7/1997 | Li |
| 5,490,750 A | 2/1996 | Gundy | | 5,643,269 A | 7/1997 | Harle et al. |
| 5,496,331 A | 3/1996 | Xu et al. | | 5,643,273 A | 7/1997 | Clark |
| 5,496,348 A | 3/1996 | Bonutti | | 5,643,295 A | 7/1997 | Yoon |
| 5,500,000 A | 3/1996 | Feagin et al. | | 5,643,319 A | 7/1997 | Green et al. |
| 5,505,735 A | 4/1996 | Li | | 5,643,320 A | 7/1997 | Lower et al. |
| 5,505,736 A | 4/1996 | Reimels et al. | | 5,643,321 A | 7/1997 | McDevitt |
| 5,507,754 A | 4/1996 | Green et al. | | 5,645,546 A | 7/1997 | Fard |
| 5,520,691 A | 5/1996 | Branch | | 5,645,547 A | 7/1997 | Coleman |
| 5,520,694 A | 5/1996 | Dance et al. | | 5,645,568 A | 7/1997 | Chervitz et al. |
| 5,520,700 A | 5/1996 | Beyar et al. | | 5,645,588 A | 7/1997 | Graf et al. |
| 5,520,702 A | 5/1996 | Sauer et al. | | 5,647,874 A | 7/1997 | Hayhurst |
| 5,522,817 A | 6/1996 | Sander et al. | | 5,649,959 A | 7/1997 | Hannam et al. |
| 5,522,820 A | 6/1996 | Caspari et al. | | 5,649,963 A | 7/1997 | McDevitt |
| 5,522,843 A | 6/1996 | Zang | | 5,658,289 A | 8/1997 | Boucher et al. |
| 5,522,844 A | 6/1996 | Johnson | | 5,658,299 A | 8/1997 | Hart |
| 5,522,845 A | 6/1996 | Wenstrom, Jr. | | 5,658,313 A | 8/1997 | Thal |
| 5,522,846 A | 6/1996 | Bonutti | | 5,662,658 A | 9/1997 | Wenstrom, Jr. |
| 5,524,946 A | 6/1996 | Thompson | | 5,662,663 A | 9/1997 | Shallman |
| 5,527,321 A | 6/1996 | Hinchliffe | | 5,662,681 A | 9/1997 | Nash et al. |
| 5,527,342 A | 6/1996 | Pietrzak et al. | | 5,665,112 A | 9/1997 | Thal |
| 5,527,343 A | 6/1996 | Bonutti | | 5,667,513 A | 9/1997 | Torrie et al. |
| 5,531,759 A | 7/1996 | Kensey et al. | | 5,671,695 A | 9/1997 | Schroeder |
| 5,534,012 A | 7/1996 | Bonutti | | 5,674,224 A | 10/1997 | Howell et al. |
| 5,536,270 A | 7/1996 | Songer et al. | | 5,679,723 A | 10/1997 | Cooper et al. |
| 5,540,698 A | 7/1996 | Preissman | | 5,681,334 A | 10/1997 | Evans et al. |
| 5,540,703 A | 7/1996 | Barker, Jr. et al. | | 5,681,352 A | 10/1997 | Clancy, III et al. |
| 5,540,718 A | 7/1996 | Bartlett | | 5,683,419 A | 11/1997 | Thal |
| 5,545,168 A | 8/1996 | Burke | | 5,688,284 A | 11/1997 | Chervitz et al. |
| 5,545,178 A | 8/1996 | Kensey et al. | | 5,688,285 A | 11/1997 | Yamada et al. |
| 5,545,180 A | 8/1996 | Le et al. | | 5,690,655 A | 11/1997 | Hart et al. |
| 5,545,228 A | 8/1996 | Kambin | | 5,690,676 A | 11/1997 | DiPoto et al. |
| 5,549,613 A | 8/1996 | Goble et al. | | 5,690,678 A | 11/1997 | Johnson |
| 5,549,617 A | 8/1996 | Green et al. | | 5,693,046 A | 12/1997 | Songer et al. |
| 5,549,619 A | 8/1996 | Peters et al. | | 5,695,497 A | 12/1997 | Stahelin et al. |
| 5,549,630 A | 8/1996 | Bonutti | | 5,697,929 A | 12/1997 | Mellinger |
| 5,549,631 A | 8/1996 | Bonutti | | 5,699,657 A * | 12/1997 | Paulson ........................... 57/22 |
| 5,562,668 A | 10/1996 | Johnson | | 5,702,397 A | 12/1997 | Goble et al. |
| 5,562,669 A | 10/1996 | McGuire | | 5,702,422 A | 12/1997 | Stone |
| 5,562,683 A | 10/1996 | Chan | | 5,702,462 A | 12/1997 | Oberlander |
| 5,562,685 A | 10/1996 | Mollenauer et al. | | 5,707,373 A | 1/1998 | Sevrain et al. |
| 5,562,686 A | 10/1996 | Sauer et al. | | 5,711,969 A | 1/1998 | Patel et al. |
| 5,569,269 A | 10/1996 | Hart et al. | | 5,713,005 A | 1/1998 | Proebsting |
| 5,569,305 A | 10/1996 | Bonutti | | 5,713,897 A | 2/1998 | Goble et al. |
| 5,570,706 A | 11/1996 | Howell | | 5,713,904 A | 2/1998 | Errico et al. |
| 5,571,090 A | 11/1996 | Sherts | | 5,713,905 A | 2/1998 | Goble et al. |
| 5,571,104 A | 11/1996 | Li | | 5,713,921 A | 2/1998 | Bonutti |
| 5,571,139 A | 11/1996 | Jenkins, Jr. | | 5,716,359 A | 2/1998 | Ojima et al. |
| 5,572,655 A | 11/1996 | Tuljapurkar et al. | | 5,716,397 A | 2/1998 | Myers |
| 5,573,286 A | 11/1996 | Rogozinski | | 5,718,717 A | 2/1998 | Bonutti |
| 5,573,542 A | 11/1996 | Stevens | | 5,720,747 A | 2/1998 | Burke |
| 5,573,548 A | 11/1996 | Nazre et al. | | 5,720,765 A | 2/1998 | Thal |
| 5,577,299 A | 11/1996 | Thompson et al. | | 5,720,766 A | 2/1998 | Zang et al. |
| 5,578,057 A | 11/1996 | Wenstrom, Jr. | | 5,722,976 A | 3/1998 | Brown |
| 5,584,695 A | 12/1996 | Lal Sachdeva et al. | | 5,725,529 A | 3/1998 | Nicholson et al. |
| 5,584,835 A | 12/1996 | Greenfield | | 5,725,549 A | 3/1998 | Lam |
| 5,584,836 A | 12/1996 | Ballintyn et al. | | 5,725,556 A | 3/1998 | Moser et al. |
| 5,584,862 A | 12/1996 | Bonutti | | 5,725,581 A | 3/1998 | Brånemark et al. |
| 5,586,986 A | 12/1996 | Hinchliffe | | 5,725,582 A | 3/1998 | Bevan et al. |
| 5,588,575 A | 12/1996 | Davignon | | 5,726,722 A | 3/1998 | Uehara et al. |
| 5,591,180 A | 1/1997 | Hinchliffe | | 5,728,107 A | 3/1998 | Zlock et al. |
| 5,591,181 A | 1/1997 | Stone et al. | | 5,728,109 A | 3/1998 | Schulze et al. |
| 5,591,207 A | 1/1997 | Coleman | | 5,728,136 A | 3/1998 | Thal |
| 5,593,407 A | 1/1997 | Reis et al. | | 5,733,293 A | 3/1998 | Scirica et al. |
| 5,593,425 A | 1/1997 | Bonutti et al. | | 5,733,306 A | 3/1998 | Bonutti |
| 5,601,557 A | 2/1997 | Hayhurst | | 5,733,307 A | 3/1998 | Dinsdale |
| 5,601,559 A | 2/1997 | Melker et al. | | 5,735,875 A | 4/1998 | Bonutti et al. |
| 5,601,571 A | 2/1997 | Moss | | 5,741,259 A | 4/1998 | Chan |
| 5,603,716 A | 2/1997 | Morgan et al. | | 5,741,260 A | 4/1998 | Songer et al. |
| 5,607,429 A | 3/1997 | Hayano et al. | | 5,741,281 A | 4/1998 | Martin et al. |

| | | | | | | |
|---|---|---|---|---|---|---|
| 5,743,912 A | 4/1998 | Lahille et al. | | 5,947,915 A | 9/1999 | Thibodo, Jr. |
| 5,746,751 A | 5/1998 | Sherts | | 5,947,982 A | 9/1999 | Duran |
| 5,746,752 A | 5/1998 | Burkhart | | 5,947,999 A | 9/1999 | Groiso |
| 5,746,754 A | 5/1998 | Chan | | 5,948,002 A | 9/1999 | Bonutti |
| 5,749,898 A | 5/1998 | Schulze et al. | | 5,951,559 A | 9/1999 | Burkhart |
| 5,755,729 A | 5/1998 | de la Torre et al. | | 5,951,560 A | 9/1999 | Simon et al. |
| 5,755,791 A | 5/1998 | Whitson et al. | | 5,954,747 A | 9/1999 | Clark |
| 5,766,176 A | 6/1998 | Duncan | | 5,957,953 A | 9/1999 | DiPoto et al. |
| 5,766,218 A | 6/1998 | Arnott | | 5,961,520 A | 10/1999 | Beck, Jr. et al. |
| 5,766,250 A | 6/1998 | Chervitz et al. | | 5,961,521 A | 10/1999 | Roger et al. |
| 5,769,894 A | 6/1998 | Ferragamo | | 5,961,524 A | 10/1999 | Crombie |
| 5,769,899 A | 6/1998 | Schwartz et al. | | 5,964,764 A | 10/1999 | West, Jr. et al. |
| 5,772,673 A | 6/1998 | Cuny et al. | | 5,964,767 A | 10/1999 | Tapia et al. |
| 5,776,196 A | 7/1998 | Matsuzaki et al. | | 5,964,769 A | 10/1999 | Wagner et al. |
| 5,782,845 A | 7/1998 | Shewchuk | | 5,964,783 A | 10/1999 | Grafton et al. |
| 5,782,862 A | 7/1998 | Bonutti | | 5,968,045 A | 10/1999 | Frazier |
| 5,782,864 A | 7/1998 | Lizardi | | 5,968,047 A | 10/1999 | Reed |
| 5,782,866 A | 7/1998 | Wenstrom, Jr. | | 5,968,077 A | 10/1999 | Wojciechowicz et al. |
| 5,785,714 A | 7/1998 | Morgan et al. | | 5,970,697 A * | 10/1999 | Jacobs et al. ................ 57/22 |
| 5,792,142 A | 8/1998 | Galitzer | | 5,972,006 A | 10/1999 | Sciaino, Jr. |
| 5,792,149 A | 8/1998 | Sherts et al. | | 5,976,125 A | 11/1999 | Graham |
| 5,796,127 A | 8/1998 | Hayafuji et al. | | 5,976,127 A | 11/1999 | Lax |
| 5,797,915 A | 8/1998 | Pierson, III et al. | | 5,980,473 A | 11/1999 | Korakianitis et al. |
| 5,797,916 A | 8/1998 | McDowell | | 5,980,524 A | 11/1999 | Justin et al. |
| 5,797,928 A | 8/1998 | Kogasaka | | 5,980,539 A | 11/1999 | Kontos |
| 5,800,407 A | 9/1998 | Eldor et al. | | 5,980,558 A | 11/1999 | Wiley |
| 5,810,824 A | 9/1998 | Chan | | 5,980,559 A | 11/1999 | Bonutti |
| 5,810,848 A | 9/1998 | Hayhurst | | 5,989,252 A * | 11/1999 | Fumex ................ 606/232 |
| 5,814,056 A * | 9/1998 | Prosst et al. ................ 606/151 | | 5,989,256 A | 11/1999 | Kuslich et al. |
| 5,814,069 A | 9/1998 | Schulze et al. | | 5,989,282 A | 11/1999 | Bonutti |
| 5,814,070 A | 9/1998 | Borzone et al. | | 5,993,452 A | 11/1999 | Vandewalle |
| 5,814,072 A | 9/1998 | Bonutti | | 5,993,476 A | 11/1999 | Groiso |
| 5,814,073 A | 9/1998 | Bonutti | | 5,997,542 A | 12/1999 | Burke |
| 5,823,980 A | 10/1998 | Kopfer | | 5,997,552 A | 12/1999 | Person et al. |
| 5,824,011 A | 10/1998 | Stone et al. | | 5,997,575 A | 12/1999 | Whitson et al. |
| 5,824,066 A | 10/1998 | Gross | | 6,001,100 A | 12/1999 | Sherman et al. |
| 5,830,234 A | 11/1998 | Wojciechowicz et al. | | 6,001,106 A | 12/1999 | Ryan et al. |
| 5,843,084 A | 12/1998 | Hart et al. | | 6,007,538 A | 12/1999 | Levin |
| 5,845,645 A | 12/1998 | Bonutti | | 6,007,567 A | 12/1999 | Bonutti |
| 5,846,254 A | 12/1998 | Schulze et al. | | 6,010,525 A | 1/2000 | Bonutti et al. |
| 5,848,983 A | 12/1998 | Basaj et al. | | 6,016,727 A | 1/2000 | Morgan |
| 5,849,012 A | 12/1998 | Abboudi | | 6,019,767 A | 2/2000 | Howell |
| 5,860,973 A | 1/1999 | Michelson | | 6,022,352 A | 2/2000 | Vandewalle |
| 5,860,978 A | 1/1999 | McDevitt et al. | | 6,022,373 A | 2/2000 | Li |
| 5,868,740 A | 2/1999 | LeVeen et al. | | 6,024,758 A | 2/2000 | Thal |
| 5,868,748 A | 2/1999 | Burke | | 6,027,523 A | 2/2000 | Schmieding |
| 5,868,789 A | 2/1999 | Huebner | | 6,030,410 A | 2/2000 | Zurbrugg |
| 5,871,484 A | 2/1999 | Spievack et al. | | 6,033,429 A | 3/2000 | Magovern |
| 5,871,486 A | 2/1999 | Huebner et al. | | 6,033,430 A | 3/2000 | Bonutti |
| 5,871,490 A | 2/1999 | Schulze et al. | | 6,039,753 A | 3/2000 | Meislin |
| 5,885,294 A | 3/1999 | Pedlick et al. | | 6,041,485 A | 3/2000 | Pedlick et al. |
| 5,891,168 A | 4/1999 | Thal | | 6,042,601 A | 3/2000 | Smith |
| 5,893,592 A | 4/1999 | Schulze et al. | | 6,045,551 A | 4/2000 | Bonutti |
| 5,895,395 A | 4/1999 | Yeung | | 6,045,571 A | 4/2000 | Hill et al. |
| 5,897,564 A | 4/1999 | Schulze et al. | | 6,045,572 A | 4/2000 | Johnson et al. |
| 5,897,574 A | 4/1999 | Bonutti | | 6,045,573 A | 4/2000 | Wenstrom, Jr. et al. |
| 5,899,902 A | 5/1999 | Brown et al. | | 6,045,574 A | 4/2000 | Thal |
| 5,899,938 A | 5/1999 | Sklar et al. | | 6,047,826 A | 4/2000 | Kalinski et al. |
| 5,908,421 A | 6/1999 | Beger et al. | | 6,048,343 A | 4/2000 | Mathis et al. |
| 5,908,436 A | 6/1999 | Cuschieri et al. | | 6,051,006 A | 4/2000 | Shluzas et al. |
| 5,910,148 A | 6/1999 | Reimels et al. | | 6,051,007 A | 4/2000 | Hogendijk et al. |
| 5,911,721 A | 6/1999 | Nicholson et al. | | 6,053,916 A | 4/2000 | Moore |
| 5,918,604 A | 7/1999 | Whelan | | 6,053,921 A | 4/2000 | Wagner et al. |
| 5,921,986 A | 7/1999 | Bonutti | | 6,056,752 A | 5/2000 | Roger |
| 5,925,008 A | 7/1999 | Douglas | | 6,056,772 A | 5/2000 | Bonutti |
| 5,928,231 A | 7/1999 | Klein et al. | | 6,056,773 A | 5/2000 | Bonutti |
| 5,928,267 A | 7/1999 | Bonutti et al. | | 6,059,817 A | 5/2000 | Bonutti et al. |
| RE36,289 E | 8/1999 | Le et al. | | 6,059,818 A | 5/2000 | Johnson et al. |
| 5,931,838 A | 8/1999 | Vito | | 6,062,344 A | 5/2000 | Okabe et al. |
| 5,931,844 A | 8/1999 | Thompson et al. | | 6,066,173 A | 5/2000 | McKernan et al. |
| 5,931,869 A | 8/1999 | Boucher et al. | | 6,068,648 A | 5/2000 | Cole et al. |
| 5,935,119 A | 8/1999 | Guy et al. | | 6,071,305 A | 6/2000 | Brown et al. |
| 5,935,133 A | 8/1999 | Wagner et al. | | 6,074,403 A | 6/2000 | Nord |
| 5,935,149 A | 8/1999 | Ek | | 6,077,277 A | 6/2000 | Mollenauer et al. |
| 5,938,668 A | 8/1999 | Scirica et al. | | 6,077,292 A | 6/2000 | Bonutti |
| 5,941,439 A | 8/1999 | Kammerer et al. | | 6,080,185 A | 6/2000 | Johnson et al. |
| 5,941,900 A | 8/1999 | Bonutti | | 6,086,591 A | 7/2000 | Bojarski |
| 5,944,739 A | 8/1999 | Zlock et al. | | 6,086,592 A | 7/2000 | Rosenberg et al. |
| 5,946,783 A | 9/1999 | Plociennik et al. | | 6,086,608 A | 7/2000 | Ek et al. |

| | | | |
|---|---|---|---|
| 6,093,200 A | 7/2000 | Liu et al. | |
| 6,096,060 A | 8/2000 | Fitts et al. | |
| 6,099,527 A | 8/2000 | Hochschuler et al. | |
| 6,099,530 A | 8/2000 | Simonian et al. | |
| 6,099,568 A | 8/2000 | Simonian et al. | |
| 6,102,934 A | 8/2000 | Li | |
| 6,106,545 A | 8/2000 | Egan | |
| 6,110,128 A | 8/2000 | Andelin et al. | |
| 6,113,604 A | 9/2000 | Whittaker et al. | |
| 6,117,160 A | 9/2000 | Bonutti | |
| 6,117,162 A | 9/2000 | Schmieding et al. | |
| 6,123,710 A | 9/2000 | Pinczewski et al. | |
| 6,132,433 A | 10/2000 | Whelan | |
| 6,132,437 A | 10/2000 | Omurtag et al. | |
| 6,139,565 A | 10/2000 | Stone et al. | |
| RE36,974 E | 11/2000 | Bonutti | |
| 6,143,017 A | 11/2000 | Thal | |
| 6,146,406 A | 11/2000 | Shluzas et al. | |
| 6,146,408 A | 11/2000 | Bartlett | |
| 6,149,653 A | 11/2000 | Deslauriers | |
| 6,149,669 A | 11/2000 | Li | |
| 6,152,928 A | 11/2000 | Wenstrom, Jr. | |
| 6,152,934 A | 11/2000 | Harper et al. | |
| 6,152,936 A | 11/2000 | Christy et al. | |
| 6,152,949 A | 11/2000 | Bonutti | |
| 6,156,039 A | 12/2000 | Thal | |
| 6,156,056 A | 12/2000 | Kearns et al. | |
| 6,159,234 A | 12/2000 | Bonutti et al. | |
| 6,165,203 A | 12/2000 | Krebs | |
| 6,168,598 B1 | 1/2001 | Martello | |
| 6,168,628 B1 | 1/2001 | Huebner | |
| 6,179,840 B1 | 1/2001 | Bowman | |
| 6,183,461 B1 | 2/2001 | Matsuura et al. | |
| 6,187,025 B1 | 2/2001 | Machek | |
| 6,190,401 B1 | 2/2001 | Green et al. | |
| 6,190,411 B1 | 2/2001 | Lo et al. | |
| 6,193,754 B1 | 2/2001 | Seedhom | |
| 6,200,318 B1 | 3/2001 | Har-Shai et al. | |
| 6,200,329 B1 | 3/2001 | Fung et al. | |
| 6,200,330 B1 | 3/2001 | Benderev et al. | |
| 6,203,556 B1 | 3/2001 | Evans et al. | |
| 6,203,565 B1 | 3/2001 | Bonutti et al. | |
| 6,203,572 B1 | 3/2001 | Johnson et al. | |
| 6,206,883 B1 | 3/2001 | Tunc | |
| 6,210,376 B1 | 4/2001 | Grayson | |
| 6,214,007 B1 | 4/2001 | Anderson | |
| 6,214,012 B1 | 4/2001 | Karpman et al. | |
| 6,217,580 B1 | 4/2001 | Levin | |
| 6,221,107 B1 | 4/2001 | Steiner et al. | |
| 6,228,096 B1 | 5/2001 | Marchand | |
| 6,231,592 B1 | 5/2001 | Bonutti et al. | |
| 6,235,057 B1 | 5/2001 | Roger et al. | |
| 6,238,395 B1 | 5/2001 | Bonutti | |
| 6,241,734 B1 | 6/2001 | Scribner et al. | |
| 6,241,747 B1 | 6/2001 | Ruff | |
| 6,241,771 B1 | 6/2001 | Gresser et al. | |
| 6,245,081 B1 | 6/2001 | Bowman et al. | |
| 6,254,604 B1 | 7/2001 | Howell | |
| 6,258,091 B1 | 7/2001 | Sevrain et al. | |
| 6,267,766 B1 | 7/2001 | Burkhart | |
| 6,269,716 B1 | 8/2001 | Amis | |
| 6,270,518 B1 | 8/2001 | Pedlick et al. | |
| 6,273,890 B1 | 8/2001 | Frazier | |
| 6,280,474 B1 | 8/2001 | Cassidy et al. | |
| 6,283,973 B1 | 9/2001 | Hubbard et al. | |
| 6,283,996 B1 | 9/2001 | Chervitz et al. | |
| 6,287,307 B1 | 9/2001 | Abboudi | |
| 6,287,325 B1 | 9/2001 | Bonutti | |
| 6,293,961 B2 | 9/2001 | Schwartz et al. | |
| 6,296,659 B1 | 10/2001 | Foerster | |
| 6,299,615 B1 | 10/2001 | Huebner | |
| 6,302,888 B1 | 10/2001 | Mellinger et al. | |
| 6,302,899 B1 | 10/2001 | Johnson et al. | |
| 6,306,156 B1 | 10/2001 | Clark | |
| 6,306,159 B1 | 10/2001 | Schwartz et al. | |
| 6,309,405 B1 | 10/2001 | Bonutti | |
| 6,312,448 B1 | 11/2001 | Bonutti | |
| 6,315,788 B1 | 11/2001 | Roby | |
| 6,319,271 B1 | 11/2001 | Schwartz et al. | |
| 6,328,758 B1 | 12/2001 | Tornier et al. | |
| 6,342,060 B1 | 1/2002 | Adams | |
| 6,343,531 B2 | 2/2002 | Amis | |
| 6,355,066 B1 | 3/2002 | Kim | |
| 6,358,270 B1 | 3/2002 | Lemer | |
| 6,364,897 B1 | 4/2002 | Bonutti | |
| 6,368,322 B1 | 4/2002 | Luks et al. | |
| 6,368,326 B1 | 4/2002 | Dakin et al. | |
| 6,368,343 B1 | 4/2002 | Bonutti et al. | |
| 6,371,124 B1 | 4/2002 | Whelan | |
| 6,379,361 B1 | 4/2002 | Beck, Jr. et al. | |
| 6,383,190 B1 | 5/2002 | Preissman | |
| 6,383,199 B2 | 5/2002 | Carter et al. | |
| 6,387,113 B1 | 5/2002 | Hawkins et al. | |
| 6,387,129 B2 | 5/2002 | Rieser et al. | |
| 6,391,030 B1 | 5/2002 | Wagner et al. | |
| 6,398,785 B2 | 6/2002 | Carchidi et al. | |
| 6,406,479 B1 | 6/2002 | Justin et al. | |
| 6,409,743 B1 | 6/2002 | Fenton, Jr. | |
| 6,413,260 B1 | 7/2002 | Berrevoets et al. | |
| 6,423,073 B2 | 7/2002 | Bowman | |
| 6,423,088 B1 | 7/2002 | Fenton, Jr. | |
| 6,428,562 B2 | 8/2002 | Bonutti | |
| 6,432,123 B2 | 8/2002 | Schwartz et al. | |
| 6,436,123 B1 | 8/2002 | Magovern | |
| 6,436,124 B1 | 8/2002 | Anderson et al. | |
| 6,440,134 B1 | 8/2002 | Zaccherotti et al. | |
| 6,440,136 B1 | 8/2002 | Gambale et al. | |
| 6,447,516 B1 | 9/2002 | Bonutti | |
| 6,451,030 B2 | 9/2002 | Li et al. | |
| 6,454,768 B1 | 9/2002 | Jackson | |
| 6,458,134 B1 | 10/2002 | Songer et al. | |
| 6,461,373 B2 | 10/2002 | Wyman et al. | |
| 6,464,713 B2 | 10/2002 | Bonutti | |
| 6,468,293 B2 | 10/2002 | Bonutti et al. | |
| 6,471,707 B1 | 10/2002 | Miller et al. | |
| 6,475,230 B1 | 11/2002 | Bonutti et al. | |
| 6,478,753 B2 | 11/2002 | Reay-Young | |
| 6,482,210 B1 | 11/2002 | Skiba et al. | |
| 6,485,504 B1 | 11/2002 | Johnson et al. | |
| 6,491,714 B1 | 12/2002 | Bennett | |
| 6,497,901 B1 | 12/2002 | Royer | |
| 6,500,184 B1 | 12/2002 | Chan et al. | |
| 6,500,195 B2 | 12/2002 | Bonutti | |
| RE37,963 E | 1/2003 | Thal | |
| 6,503,267 B2 | 1/2003 | Bonutti et al. | |
| 6,506,190 B1 | 1/2003 | Walshe | |
| 6,508,820 B2 | 1/2003 | Bales | |
| 6,508,821 B1 | 1/2003 | Schwartz et al. | |
| 6,508,830 B2 | 1/2003 | Steiner | |
| 6,511,498 B1 * | 1/2003 | Fumex | 606/232 |
| 6,511,499 B2 | 1/2003 | Schmieding et al. | |
| 6,517,542 B1 | 2/2003 | Papay et al. | |
| 6,517,552 B1 | 2/2003 | Nord et al. | |
| 6,517,564 B1 | 2/2003 | Grafton et al. | |
| 6,517,578 B2 | 2/2003 | Hein | |
| 6,517,579 B1 | 2/2003 | Paulos et al. | |
| 6,520,964 B2 | 2/2003 | Tallarida et al. | |
| 6,520,980 B1 | 2/2003 | Foerster | |
| 6,524,317 B1 | 2/2003 | Ritchart et al. | |
| 6,527,777 B2 | 3/2003 | Justin | |
| 6,527,794 B1 | 3/2003 | McDevitt et al. | |
| 6,527,795 B1 | 3/2003 | Lizardi | |
| 6,533,795 B1 | 3/2003 | Tran et al. | |
| 6,533,802 B2 | 3/2003 | Bojarski et al. | |
| 6,537,319 B2 | 3/2003 | Whelan | |
| 6,540,750 B2 | 4/2003 | Burkhart | |
| 6,540,769 B1 | 4/2003 | Miller, III | |
| 6,540,770 B1 | 4/2003 | Tornier et al. | |
| 6,540,783 B1 | 4/2003 | Whittaker et al. | |
| 6,544,281 B2 | 4/2003 | ElAttrache et al. | |
| 6,547,564 B1 | 4/2003 | Hansson et al. | |
| 6,547,778 B1 | 4/2003 | Sklar et al. | |
| 6,547,800 B2 | 4/2003 | Foerster et al. | |
| 6,551,330 B1 | 4/2003 | Bain et al. | |
| 6,551,343 B1 | 4/2003 | Tormala et al. | |
| 6,553,802 B1 | 4/2003 | Jacob et al. | |
| 6,554,830 B1 | 4/2003 | Chappius | |
| 6,554,852 B1 | 4/2003 | Oberlander | |

| | | |
|---|---|---|
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,648,921 B2 * | 11/2003 | Anderson et al. .......... 623/23.64 |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B2 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 * | 8/2005 | Morgan et al. ................ 606/232 |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B2 | 2/2007 | Andrews |
| 7,201,722 B2 | 4/2007 | Krueger |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |

| | | |
|---|---|---|
| 7,303,577 B1 | 12/2007 | Dean |
| 7,306,417 B2 * | 12/2007 | Dorstewitz .................... 410/100 |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 * | 6/2010 | Ken .................... 606/213 |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,162,997 B2 | 4/2012 | Struhl |
| 8,167,906 B2 | 5/2012 | Cauldwell et al. |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,409,253 B2 | 4/2013 | Stone et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 * | 11/2001 | Hein .................... 623/13.13 |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 * | 3/2002 | Foerster .................... 606/228 |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |

| Publication No. | Date | Inventor(s) |
|---|---|---|
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 * | 10/2004 | Sikora et al. .................. 606/151 |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 * | 6/2005 | Fallman ........................ 606/213 |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |

| | | |
|---|---|---|
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1* | 12/2006 | Bojarski et al. ............... 606/232 |
| 2007/0005080 A1 | 1/2007 | Wolniewicz et al. |
| 2007/0010857 A1* | 1/2007 | Sugimoto et al. ............. 606/232 |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1* | 1/2009 | Brunelle et al. ........... 623/13.19 |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1* | 9/2009 | Arcenio et al. ............ 623/17.16 |
| 2009/0248091 A1 | 10/2009 | Teague et al. |
| 2009/0265014 A1 | 10/2009 | May et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |

| | | | | | | |
|---|---|---|---|---|---|---|
| 2012/0165867 | A1 | 6/2012 | Denham et al. | EP | 991210527 | 10/1999 |
| 2012/0165938 | A1 | 6/2012 | Denham et al. | EP | 0995409 | 4/2000 |
| 2012/0197271 | A1 | 8/2012 | Astorino et al. | EP | 1013229 | 6/2000 |
| 2012/0245585 | A1 | 9/2012 | Kaiser et al. | EP | 1093773 | 4/2001 |
| 2012/0296427 | A1 | 11/2012 | Conner et al. | EP | 1093774 | 4/2001 |
| 2012/0310245 | A1 | 12/2012 | Hoeppner et al. | EP | 1555945 | 7/2005 |
| 2013/0023930 | A1 | 1/2013 | Stone et al. | EP | 2238944 A2 | 10/2010 |
| 2013/0035698 | A1 | 2/2013 | Stone et al. | EP | 2544607 A1 | 1/2013 |
| 2013/0046341 | A1 | 2/2013 | Stone et al. | FR | 2622790 | 5/1989 |
| 2013/0103082 | A1 | 4/2013 | Kaiser et al. | FR | 2655840 | 6/1991 |
| 2013/0110251 | A1 | 5/2013 | Metzger et al. | FR | 2682867 | 4/1993 |
| 2013/0116730 | A1 | 5/2013 | Denham et al. | FR | 2687911 | 9/1993 |
| 2013/0123813 | A1 | 5/2013 | Stone et al. | FR | 2688689 | 9/1993 |

FOREIGN PATENT DOCUMENTS

| | | | | | |
|---|---|---|---|---|---|
| | | | FR | 2704140 | 10/1994 |
| | | | FR | 2717070 | 9/1995 |
| | | | FR | 2723528 | 2/1996 |
| AU | 4957264 | 3/1966 | FR | 2744010 | 8/1997 |
| AU | 440266 | 10/1967 | FR | 2745999 | 9/1997 |
| AU | 5850469 | 1/1971 | FR | 2770764 | 5/1999 |
| AU | 5963869 | 2/1971 | GB | 401677 | 11/1933 |
| AU | 1505470 | 11/1971 | GB | 1413477 | 11/1975 |
| AU | 2223767 | 5/1973 | GB | 1485681 | 9/1977 |
| AU | 3615171 | 5/1973 | GB | 2083751 | 3/1982 |
| AU | 5028569 | 9/1973 | GB | 2118474 | 11/1983 |
| AU | 7110887 | 10/1987 | GB | 2227175 | 7/1990 |
| AU | 639410 | 11/1989 | GB | 2253147 A | 9/1992 |
| AU | 651929 | 8/1994 | GB | 2312376 | 10/1997 |
| DE | 2529669 | 3/1976 | GB | 2403416 A | 1/2005 |
| DE | 2747312 | 4/1979 | JP | 5362911 | 5/1978 |
| DE | 2818254 | 10/1979 | JP | 5362912 | 5/1978 |
| DE | 2919009 | 11/1979 | JP | 5374942 | 6/1978 |
| DE | 3027138 | 12/1981 | JP | 5378230 | 6/1978 |
| DE | 3225620 | 2/1983 | JP | 62159647 | 7/1987 |
| DE | 3136083 | 3/1983 | JP | 62295657 | 12/1987 |
| DE | 233303 | 2/1986 | JP | 5269160 | 10/1993 |
| DE | 4127550 | 2/1993 | JP | 5300917 | 11/1993 |
| DE | 4302397 | 7/1993 | JP | 751292 | 2/1995 |
| DE | 29621340 | 5/1998 | JP | 10211213 | 8/1998 |
| DE | 19841252 | 3/2000 | WO | WO-8300615 | 3/1983 |
| DE | 20207781 U1 | 8/2002 | WO | WO-8603666 | 7/1986 |
| EP | 0108912 | 5/1984 | WO | WO-8701270 | 3/1987 |
| EP | 0129442 | 12/1984 | WO | WO-8901767 | 3/1989 |
| EP | 0172130 | 2/1986 | WO | WO-8909030 | 10/1989 |
| EP | 0241240 | 10/1987 | WO | WO-8910096 | 11/1989 |
| EP | 0241792 | 10/1987 | WO | WO-9008510 | 8/1990 |
| EP | 0260970 | 3/1988 | WO | WO-9203980 | 3/1992 |
| EP | 0270704 | 6/1988 | WO | WO-9314705 | 8/1993 |
| EP | 0282789 | 9/1988 | WO | WO-9315694 | 8/1993 |
| EP | 0315371 | 5/1989 | WO | WO-9502373 | 1/1995 |
| EP | 0317406 | 5/1989 | WO | WO-9503003 | 2/1995 |
| EP | 0340159 | 11/1989 | WO | WO-9529637 | 11/1995 |
| EP | 0346183 | 12/1989 | WO | WO-9532670 | 12/1995 |
| EP | 0349173 | 1/1990 | WO | WO-9609797 A1 | 4/1996 |
| EP | 0374088 | 6/1990 | WO | WO-9629029 | 9/1996 |
| EP | 0409364 | 1/1991 | WO | WO-9737603 | 10/1997 |
| EP | 0415915 | 3/1991 | WO | WO-9812991 | 4/1998 |
| EP | 0440991 | 8/1991 | WO | WO-9812992 | 4/1998 |
| EP | 0441065 | 8/1991 | WO | WO-9822047 | 5/1998 |
| EP | 0451932 | 10/1991 | WO | WO-9822048 | 5/1998 |
| EP | 0464480 | 1/1992 | WO | WO-9901084 | 1/1999 |
| EP | 0497079 | 8/1992 | WO | WO-9912480 | 3/1999 |
| EP | 0502509 | 9/1992 | WO | WO-9937219 A1 | 7/1999 |
| EP | 0502698 | 9/1992 | WO | WO-9944544 | 9/1999 |
| EP | 520177 | 12/1992 | WO | WO-9952472 A1 | 10/1999 |
| EP | 0546726 | 6/1993 | WO | WO-0040159 | 7/2000 |
| EP | 0574707 | 12/1993 | WO | WO-0139671 | 6/2001 |
| EP | 0582514 | 2/1994 | WO | WO-0236020 | 5/2002 |
| EP | 0591991 | 4/1994 | WO | WO-03005914 A1 | 1/2003 |
| EP | 0598219 | 5/1994 | WO | WO-03071962 | 9/2003 |
| EP | 0611551 A1 | 8/1994 | WO | WO-03077772 | 9/2003 |
| EP | 0627203 | 12/1994 | WO | WO-03092551 A1 | 11/2003 |
| EP | 0651979 | 5/1995 | WO | WO-2004091412 A1 | 10/2004 |
| EP | 0669110 | 8/1995 | WO | WO-2005104992 A1 | 11/2005 |
| EP | 0686373 | 12/1995 | WO | WO-2006023661 A2 | 3/2006 |
| EP | 0702933 | 3/1996 | WO | WO-2006055823 A2 | 5/2006 |
| EP | 0775473 | 5/1997 | WO | WO-2007045460 A2 | 4/2007 |
| EP | 0913123 | 5/1999 | WO | WO-2007109280 A2 | 9/2007 |
| EP | 0913131 | 5/1999 | WO | WO-2008002550 A2 | 1/2008 |
| EP | 99121106 | 10/1999 | WO | WO-2008015171 A1 | 2/2008 |

| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |

OTHER PUBLICATIONS

"Arthroscopic Meniscal Repair using the Meniscal Cinch™", Surgical Technique brochure. (2008) Arthrex® 6 sheets.
Interview Summary mailed Jul. 14, 2011 for U.S. Appl. No. 12/196,407.
Interview Summary mailed Jul. 14, 2011 for U.S. Appl. No. 12/196,410.
Notice of Allowance mailed Oct. 13, 2011 for U.S. Appl. No. 12/196,410.
Notice of Allowance mailed Oct. 26, 2011 for U.S. Appl. No. 12/196,407.
Notice of Allowance mailed Mar. 22, 2012 for U.S. Appl. No. 13/102,182.
Notice of Allowance mailed Jun. 1, 2009 for U.S. Appl. No. 11/541,506.
Notice of Allowance mailed Sep. 18, 2009 for U.S. Appl. No. 11/541,505.
Office Action mailed Dec. 7, 2011 for U.S. Appl. No. 12/589,168.
Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
"AperFix® System Surgical Technique Guide. Single Tunnel Double Bundle.™" Cayenne Medical brochure. (Aug. 2008) 8 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jul. 19, 2012, for PCT/US2012/037703 claiming benefit of U.S. Appl. No. 13/109,667, filed May 7, 2011.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
Interview Summary mailed Jun. 20, 2011 for U.S. Appl. No. 12/196,405.
Notice of Allowance (Supplemental Notice of Allowability) mailed Apr. 15, 2011 for U.S. Appl. No. 12/196,398 filed Aug. 22, 2008; now U.S. Patent No. 7,959,650.
Notice of Allowance (Supplemental Notice of Allowability) mailed Mar. 9, 2011 for U.S. Appl. No. 12/196,398, filed Aug. 22, 2008; now U.S. Patent No. 7,959,650.
Notice of Allowance mailed Oct. 26, 2011 for U.S. Appl. No. 12/196,405.
Notice of Allowance mailed Jun. 1, 2009 for U.S. Appl. No. 11/541,506 filed Sep. 29, 2006; now U.S. Patent No. 7,601,165.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398, filed Aug. 22, 2010; now U.S. Patent No. 7,959,650.
Office Action from the U.S. Patent Office mailed Mar. 5, 2013 for U.S. Appl. No. 12/702,067.
Office Action from the U.S. Patent Office mailed Mar. 13, 2013 for U.S. Appl. No. 13/181,729.
Office Action from the U.S. Patent Office mailed Mar. 20, 2013 for U.S. Appl. No. 13/399,125.

Office Action mailed Apr. 11, 2011 for U.S. Appl. No. 12/196,405.
Office Action mailed May 19, 2009 for U.S. Appl. No. 11/541,505, filed Sep. 29, 2006; now U.S. Patent No. 7,658,751.
Office Action mailed May 4, 2011 for U.S. Appl. No. 12/196,407, filed Aug. 22, 2008.
Office Action mailed May 9, 2011 for U.S. Appl. No. 12/196,410, filed Aug. 22, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Patent No. 7,658,751.
Restriction Requirement mailed Mar. 9, 2009 for U.S. Appl. No. 11/541,506, filed Sep. 29, 2006; now U.S. Patent No. 7,601,165.
Restriction Requirement mailed Sep. 29, 2010 for U.S. Appl. No. 12/196,398, filed Aug. 22, 2008; now U.S. Patent No. 7,959,650.
"Suture Tensioner w/Tensiometer," Arthrex® , Inc. catalog "Next Generation in Knee Ligament Reconstruction & Repair Technology," 2009.
"TriTis™ Tibial Fixation System and Implant" brochure. Scandius Biomedical (2006).
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Interview Summary mailed Nov. 27, 2012 for U.S. Appl. No. 13/098,897.
Office Action mailed Oct. 24, 2012 for U.S. Appl. No. 13/399,125.
Office Action mailed Sep. 21, 2012 for U.S. Appl. No. 13/098,897.
Office Action mailed Sep. 24, 2012 for U.S. Appl. No. 13/098,927.
Office Action mailed Oct. 2, 2012 for U.S. Appl. No. 13/181,729.
US 6,238,418, 05/2001, Schwartz et al. (withdrawn)

* cited by examiner

*Primary Examiner* — Dianne Dornbusch
(74) *Attorney, Agent, or Firm* — Harness, Dickey

(57) ABSTRACT

A self-locking adjustable loop construction and a method of forming the construction are disclosed. The construction can include a flexible member having a first end, a second end and a first portion therebetween. The first end can be passed back through the first portion at a first point such that the first end passes through the first portion from a first side of the flexible member to a second opposite side of the flexible member. The first end can be passed through the first portion at a second point spaced apart from the first point such that the first end passes through the first portion from the second side to the first side so as to place the second end outside of the first portion.

18 Claims, 14 Drawing Sheets

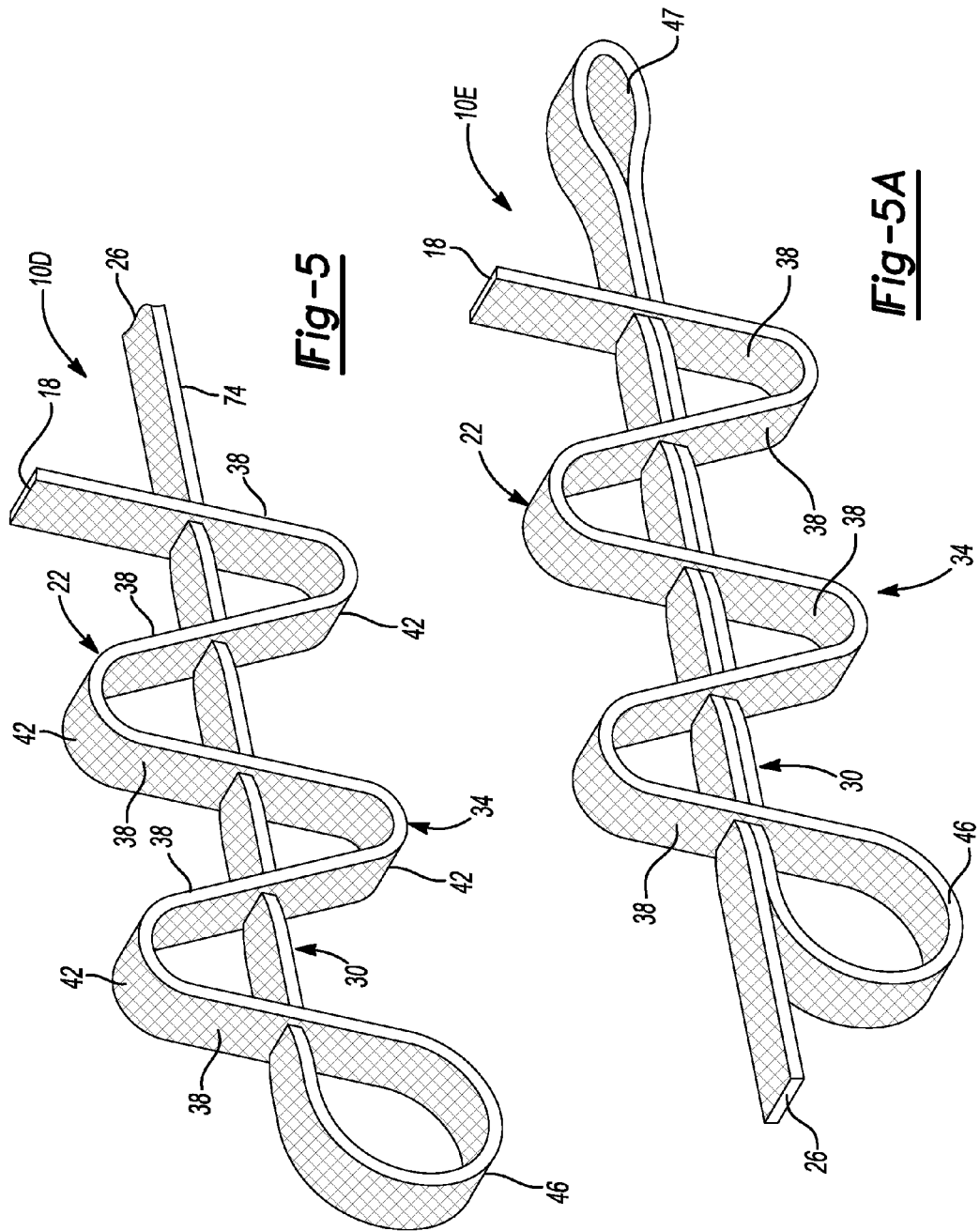

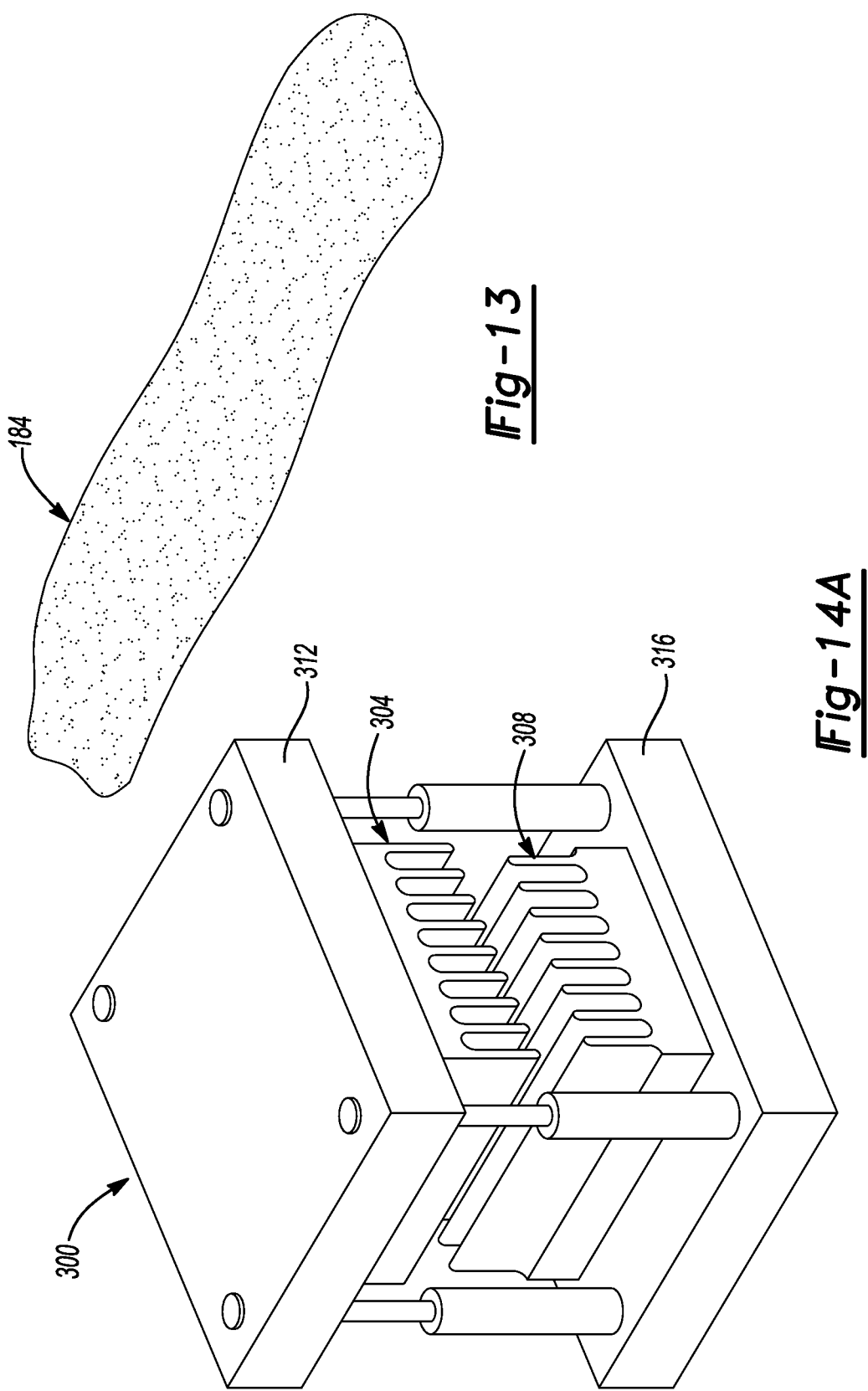

METHOD AND APPARATUS FOR FORMING A SELF-LOCKING ADJUSTABLE LOOP

CROSS-REFERENCE TO RELATED APPLICATIONS

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 12/719,337 filed on Mar. 8, 2010, which is a continuation-in-part of U.S. patent application Ser. No. 12/489,168 filed on Jun. 22, 2009 now U.S. Pat. No. 8,361,113, which is a continuation-in-part of U.S. patent application Ser. No. 12/474,802 filed on May 29, 2009, now U.S. Pat. No. 8,088,130 issued on Jan. 3, 2012, which is a continuation-in-part of (a) U.S. patent application Ser. No. 12/196,405 filed on Aug. 22, 2008, now U.S. Pat. No. 8,128,658 issued on Mar. 6, 2012; (b) U.S. patent application Ser. No. 12/196,407 filed on Aug. 22, 2008, now U.S. Pat. No. 8,137,382 issued on Mar. 20, 2012; (c) U.S. patent application Ser. No. 12/196,410 filed on Aug. 22, 2008, now U.S. Pat. No. 8,118,836 issued on Feb. 21, 2012; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, now U.S. Pat. No. 8,303,604 issued on Nov. 6, 2012, which is a continuation-in-part of U.S. patent application Ser. No. 12/014,399 filed on Jan. 15, 2008 now U.S. Pat. No. 7,909,851 issued on Mar. 22, 2011.

This application is a continuation-in-part of U.S. patent application Ser. No. 12/196,398 filed Aug. 22, 2008, now U.S. Pat. No. 7,959,650 issued on Jun. 14, 2011, which is a continuation-in-part of U.S. patent application Ser. No. 11/784,821 filed Apr. 10, 2007.

The disclosures of all of the above applications are incorporated by reference herein.

FIELD

The present disclosure relates generally to a method and apparatus for forming a self-locking adjustable loop.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors can still be made. For example, the procedure of tying knots can be very time consuming, thereby increasing the cost of the procedure and limiting the capacity of a surgeon. Furthermore, the strength of the repair may be limited by the strength of the knot. This latter drawback may be of particular significance if the knot is tied improperly as the strength of the knot in such situations can be significantly lower than the tensile strength of the suture material.

To overcome this problem, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Unfortunately, relaxation of the system may allow a portion of the suture to translate back through the passage, thus potentially relieving some of the desired tension.

It is an object of the present teachings to provide an alternative arrangement for anchoring sutures to bone and soft tissue. The arrangement, which is relatively simple in design and structure, is highly effective for its intended purpose.

SUMMARY

This section provides a general summary of the disclosure, and is not a comprehensive disclosure of its full scope or all of its features.

According to one aspect, the present teachings provide a method of forming a self-locking adjustable loop. The method can include providing a flexible member having a first end, a second end and a first portion therebetween. The first end of the flexible member can be passed back through the first portion at a first point such that the first end passes through the first portion from a first side of the flexible member to a second opposite side of the flexible member. The first end can be passed through the first portion at a second point spaced apart from the first point such that the first end passes through the first portion from the second side to the first side so as to place the second end outside of the first portion.

According to another aspect, the present teachings provide a method of forming a self-locking adjustable loop. The method can include providing a flexible member having a first end, a second end, and a first portion therebetween, and forming the flexible member into a pleated configuration having a plurality of interconnected layers each extending a length of the flexible member and orientated in a stacked relationship relative to each other. The first end of the flexible member can be passed back through the first portion at a first point such that the first end passes through the first portion from a first side of the flexible member to a second opposite side in a direction other than parallel to a longitudinal axis of the first portion. The first end can be passed through the first portion at a second point such that the first end passes through the first portion from the second side to the first side in a direction other than parallel to the longitudinal axis the of the first portion so as to place the second end outside of the first portion, the second point being spaced longitudinally from the first point.

According to yet another aspect, the present teachings provide a self-locking adjustable loop construction including a flexible member having a first end, a second end, and a first portion between the first and second ends. The first end can be passed through the first portion at a first point from a first side to a second side in a direction other than parallel to a longitudinal axis of the first portion proximate the first point. The first end can be passed through the first portion to form a self-locking adjustable loop.

In still another aspect, the present teachings provide a self-locking adjustable loop construction including a flexible member having a first end, a second end, and first and second portions between the first and second ends. The second portion can be passed through the first portion at a first point from a first side to a second side in a direction other than parallel to a longitudinal axis of the first portion to form a self-locking adjustable loop.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 2A is a view of an exemplary formation of the adjustable loop construction of FIG. 2 according to the present teachings;

FIG. 5 is a view of an exemplary alternative self-locking adjustable loop construction according to the present teachings;

FIG. 5A is a view of an exemplary alternative self-locking adjustable loop construction of FIG. 5 having two loops according to the present teachings;

FIG. 13 is a view of an exemplary graft in a pre-formed state according to the present teachings; and FIGS. 14A and 14B are views of an exemplary arrangement for forming the self-locking adjustable loop constructions of FIGS. 10 and 11 according to the present teachings.

DETAILED DESCRIPTION

Figure 1:
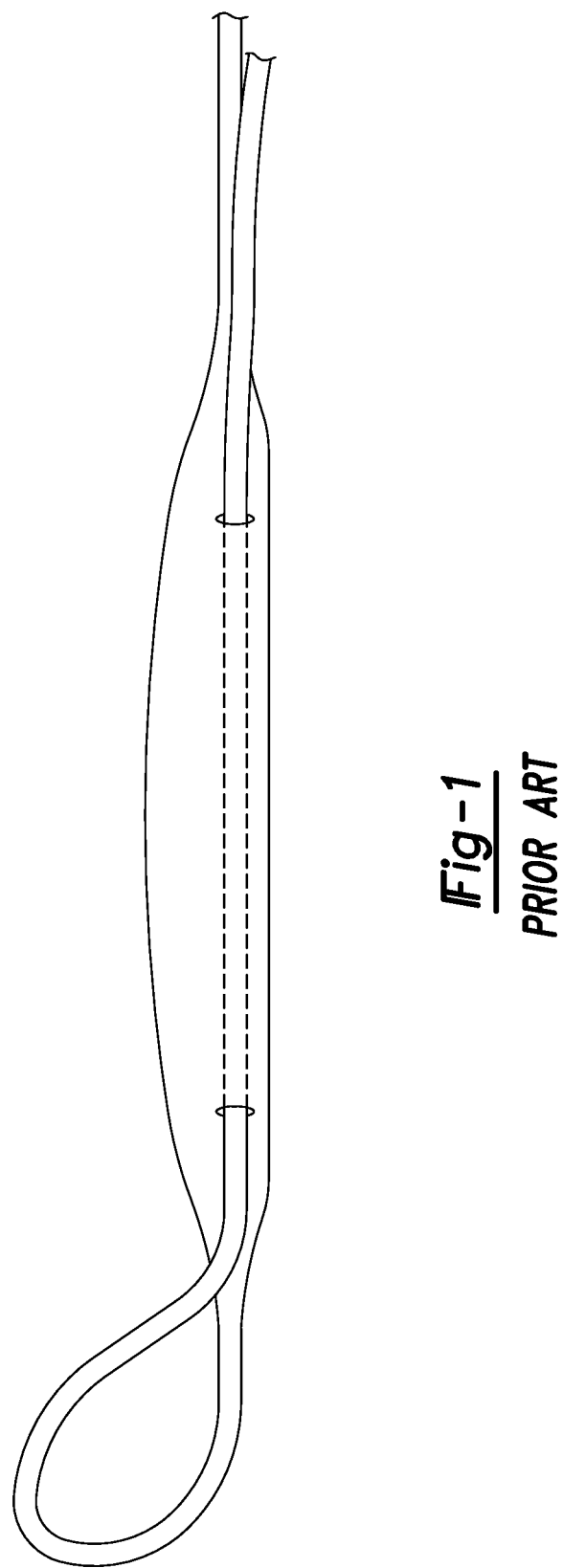
FIG. 1 is a view of a prior art suture construction.

The following description is merely exemplary in nature and is in no way intended to limit the present disclosure, its application, or uses. It should be understood that throughout the drawings, corresponding reference numerals indicate like or corresponding parts and features.

Figure 2:
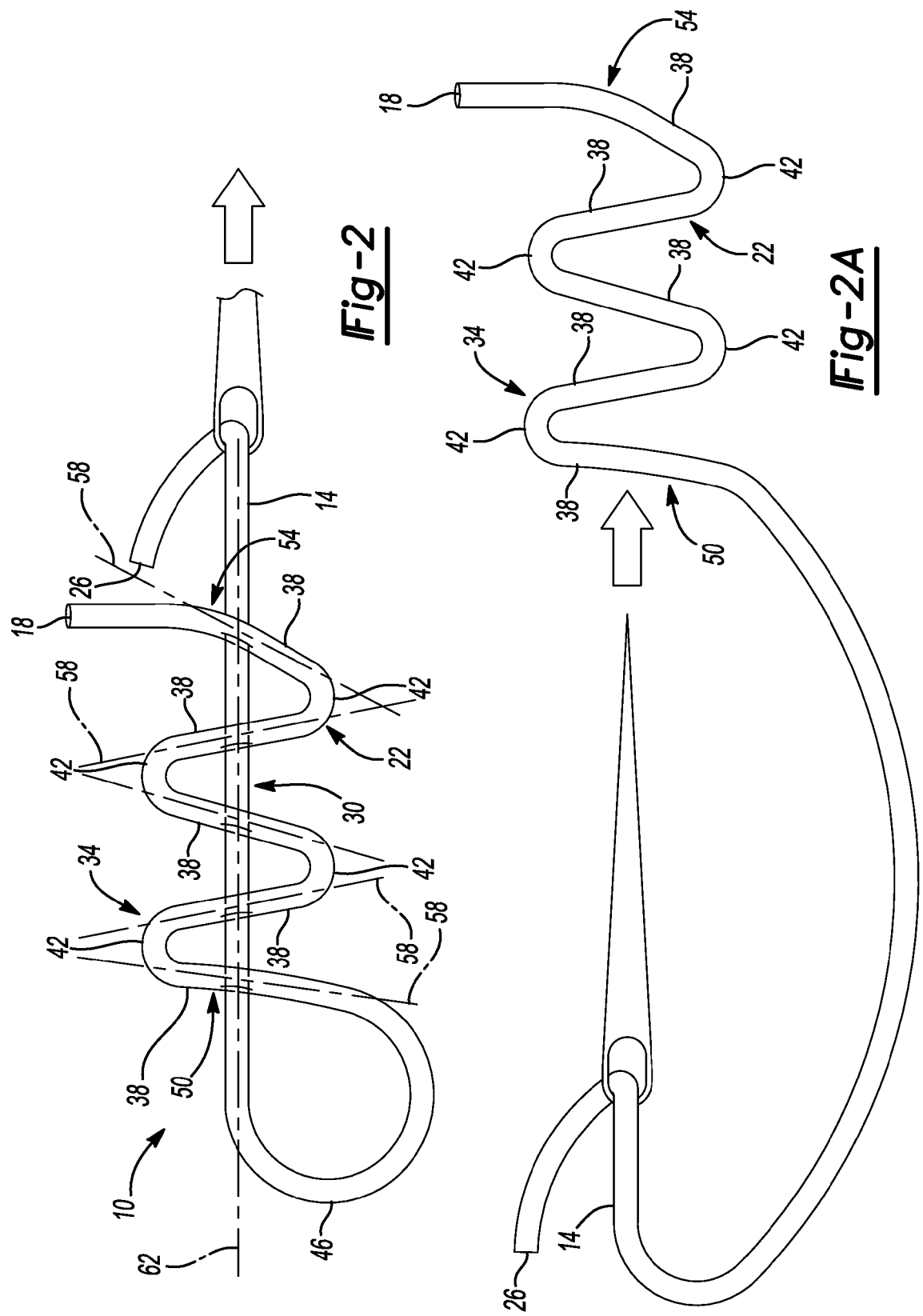
FIG. 2 is a view of an exemplary self-locking adjustable loop construction according to the present teachings.

With reference to FIGS. 2 and 2A, an adjustable self-locking loop construction 10 is provided. The adjustable loop construction 10 can include a flexible member or suture 14 having a width or diameter in cross-section sufficient to pass a section of the suture 14 back therethrough, as will be described in greater detail below. Adjustable loop construction 10 can be formed with only a single or unitary suture 14 having a solid construction or alternatively a hollow core. The suture 14 can also include a braided structure, a ribbon structure or a monofilament structure.

Suture 14 can include a first end 18, a first portion 22 proximate the first end 18, a second end 26 and a second portion 30 proximate the second end 26, as generally shown in FIG. 2. The adjustable loop construction 10 can be constructed by forming an accordion or wave-like configuration 34 with the first portion 22 of suture 14. The accordion configuration 34 can include multiple legs 38 having connecting portions 42 on opposite ends of the legs, as shown in FIG. 2. Once the accordion configuration 34 is formed, the second end 26 of the suture 14 can be passed through an aperture formed in each leg 38 or pierced through each leg 38 such that an adjustable loop 46 is formed at one end 50 of the accordion configuration 34 and the second end 26 extends beyond a second end 54 of the accordion configuration 34, as shown in FIGS. 2 and 2A.

It should be appreciated that while the above discussion references the second end 26 being passed through the accordion region being formed with the first portion 22, the first end 18 could alternatively be passed through the accordion configuration 34, which could be formed with the second portion 30. It should also be appreciated that while FIG. 2 shows the second end 26 being passed through a central portion of the legs 38, the second end 26 could be passed through various positions of legs 38 along a longitudinal axis 58 thereof.

Continuing with the exemplary illustrations in FIGS. 2 and 2A, second end 26 can be passed through each leg 38 in a direction that is not parallel to the longitudinal axes 58. In an exemplary configuration, second end 26 can be passed through each leg 38 in a direction perpendicular or substantially perpendicular to longitudinal axis 58. It should be appreciated that while the legs 38 are shown in FIG. 2 as having an orientation substantially perpendicular to a longitudinal axis 62 of the second portion 30 as it is passed therethrough, the legs 38 can include other non-parallel orientations relative to axis 62, such as 45 degrees.

With the adjustable loop 46 being formed as shown in FIGS. 2 and 2A, tension can be applied to the second end 26 of suture 14 that extends from the second end 54 of the accordion configuration 34. Upon applying tension to second end 26, the size of loop 46 can be reduced to a desired size or load. At this point, additional tension from both the loop 46 and the tension being applied to second end 26 can cause the suture 14 to constrict and thereby reduce in diameter due to the axial tensile load being applied. In addition, the legs 38, by way of their non-parallel orientation to the second portion 30, can cause a transverse force to be applied to second portion 30 once tension is applied from the loop 46 and the second portion 30.

Such reduction in diameter can cause the legs 38 to squeeze or constrict around the portions of second portion 30 passing therethrough, which creates a mechanical interface between the interior portions or apertures of the legs 38 that are constricting around the portions of the second portion 30 passing therethrough. As a result, under tension, the mechanical interface along with the transverse force applied by each leg 38 can efficiently lock the second portion 30 to the accordion configuration 34 at a desired size of loop 46.

The accordion configuration 34 can include the plurality of legs 38, as discussed above. The number of the plurality of legs 38 utilized can affect the ability of the accordion configuration 34 to provide the self-locking capability discussed above. In this regard, it should be appreciated that providing more legs 38 in the non-parallel orientation to the second portion 30 passing therethrough can provide a greater locking capability of the adjustable self-locking construction 10. In addition, for a braided suture construct, the number of weaves as well as how tightly the weaves are formed can affect the number of legs 38 that can be required to form the self-locking adjustable loop construction 10. For example, more legs 38 can be required for a braided suture construct that includes less weaves and/or is more loosely braided than a suture construct having a tightly braided structure or monofilament.

Figure 3:
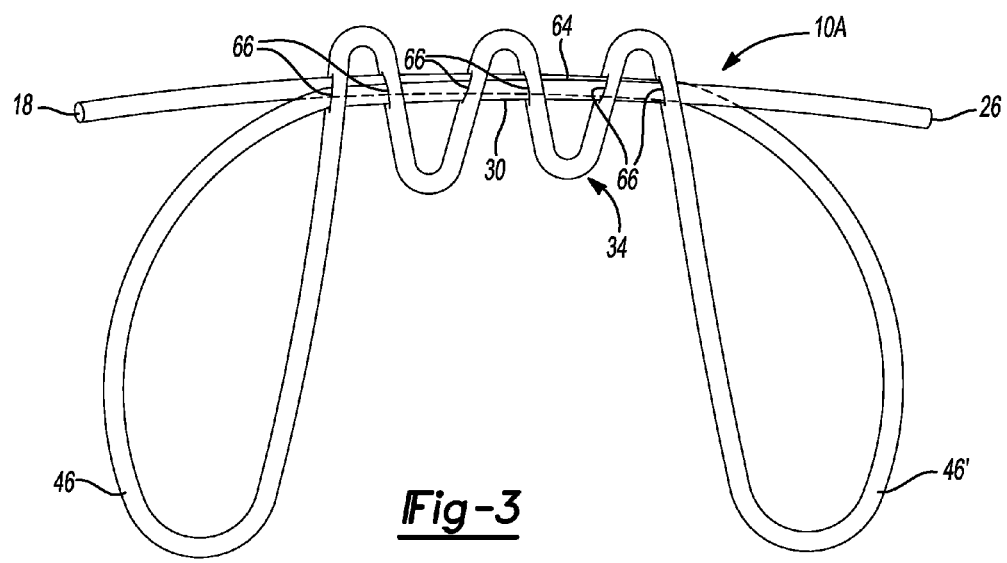
FIG. 3 is a view of an exemplary alternative construction of the self-locking adjustable loop construction of FIG. 2 having two loops according to the present teachings.
Figure 4:
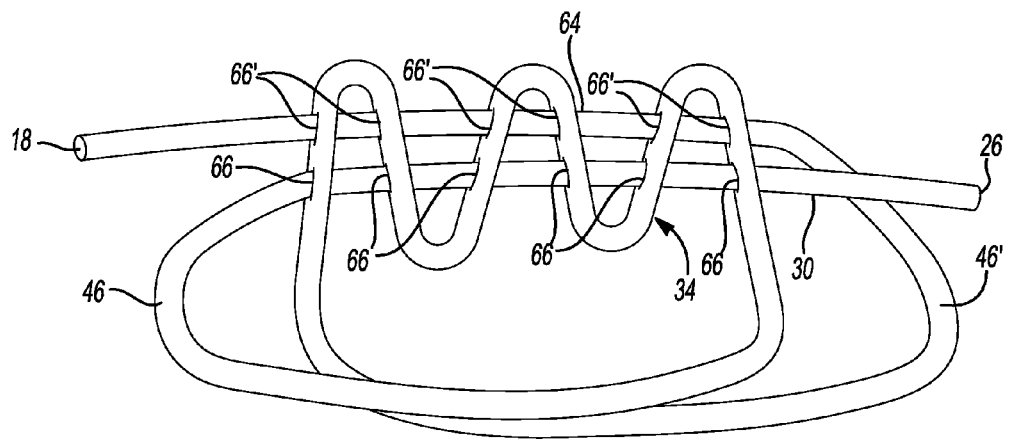
FIG. 4 is a view of an alternative construction of the self-locking adjustable loop construction of FIG. 3 according to the present teachings.

With additional reference to FIGS. 3 and 4, an alternative self-locking adjustable loop construction 10A is provided that can include an additional loop 46' thereby forming a bow tie configuration. Adjustable loop construction 10A can be formed and can function in a similar manner as adjustable loop construction 10, except two loops 46, 46' can be provided and available for securing to bone, soft tissue, or other devices. More specifically, adjustable loop construction 10A can be formed by taking first end 18 and passing it back through the legs 38 of accordion configuration 34 in an opposite axial direction as second end 26 and portion 30 were passed through the accordion configuration 34, as discussed above with reference to FIGS. 2 and 2A.

With this construction, a portion 64 of suture 14 passed through accordion configuration 34 by first end 18 can be adjacent to second potion 30, as shown in FIG. 3. In one exemplary configuration, first end 18 and portion 64 can be passed through the same aperture or opening 66 created in legs 38 by second portion 30 being passed therethrough. Alternatively, and with reference to FIG. 4, first end 18 and portion 64 can be passed through legs 38 spaced apart from second portion 30 such that portion 64 and second portion 30 form separate openings 66, 66' in legs 38.

In operation, tension can be applied to both the first and second ends 18, 26 until the corresponding loops 46, 46' are reduced to the desired size and/or load. At this point, the tension applied by the loops and the respective ends can cause the diameter reduction and transverse forces discussed above thereby creating the mechanical interface and locking the loops 46, 46' relative to the accordion configuration 34. In addition, with reference to the construction 10A shown in FIG. 3, the first and second portions can be contiguous to each other thereby causing additional friction and resistance to relative movement under tensile load.

Figure 3A:
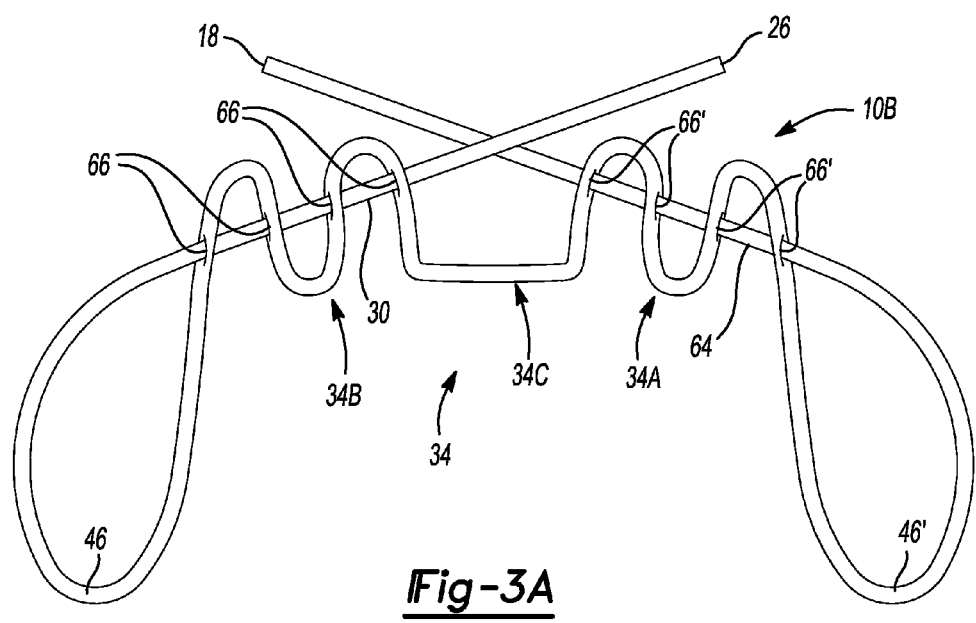
FIG. 3A is a view of an exemplary alternative construction of the self-locking adjustable loop construction of FIG. 3 according to the present teachings.

With additional reference to FIGS. 3A and 3B, alternative adjustable loop constructions 10B and 10C are shown that are similar in operation to the constructions 10A of FIGS. 3 and 4, such that only differences between the constructions will be discussed below. With particular reference to construction 10B shown in FIG. 3A, the accordion configuration 34 can be separated into first and second portions 34A and 34B by an intermediate portion 34C. First end 18 can extend through separate openings 66' in the plurality of legs 38 of the first accordion portion 34A to form adjustable loop 46'. Similarly, second end 26 can be passed through openings 66 of the plurality of legs 38 of the second accordion portion 34B to form adjustable loop 46. In this exemplary configuration, portions 30 and 64 can be configured to not overlap when passed through the respective accordion portions, as shown in FIG. 3A. It should be appreciated that while construction 10B has been discussed above as having an intermediate portion 34C, construction 10B could also be provided without the intermediate portion, similar to accordion configuration 34 shown in FIG. 3.

Figure 3B:
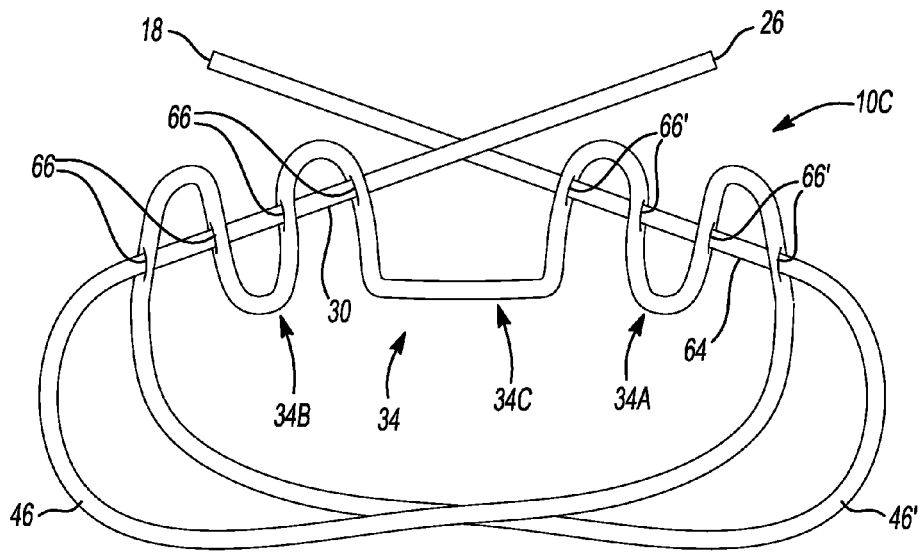
FIG. 3B is a view of another exemplary alternative construction of the self-locking adjustable loop construction of FIG. 3 according to the present teachings.

As shown in FIG. 3B, construction 10C includes an alternative loop construction to that of construction 10B shown in FIG. 3A, where loops 46, 46' are formed so as to span the accordion configuration 34 instead of being formed at opposite ends of the accordion configuration 34. In this configuration, construction 10C can form a double loop configuration where the first and second loops 46 can each traverse a path from one end of the accordion configuration 34 to the other end of the accordion configuration 34, as shown in FIG. 3B.

Turning now to FIG. 5, an alternative self-locking adjustable loop construction 10D is shown that is similar to the construction 10 of FIG. 2, except formed with a flat braid or ribbon construct 74. Adjustable loop construction 10D can be formed in the same manner as construction 10, noting that the entry and exit points of the second end 26 being passed through construct 74 are the same except on opposite sides of the braid or ribbon. With additional reference to FIG. 5A, an alternative adjustable loop construction 10E is shown that is similar to construction 10D, except that an additional loop 47 is formed using second end 26 to form an alternative double loop configuration. As shown in FIG. 5A, second end 26 can be passed back through accordion configuration 34 in a direction opposite the direction used to form loop 46 so as to form second loop 47. Second end 26 can be passed back through as discussed above using the same openings in legs 38, or different openings like shown in FIG. 4.

Figure 5B:
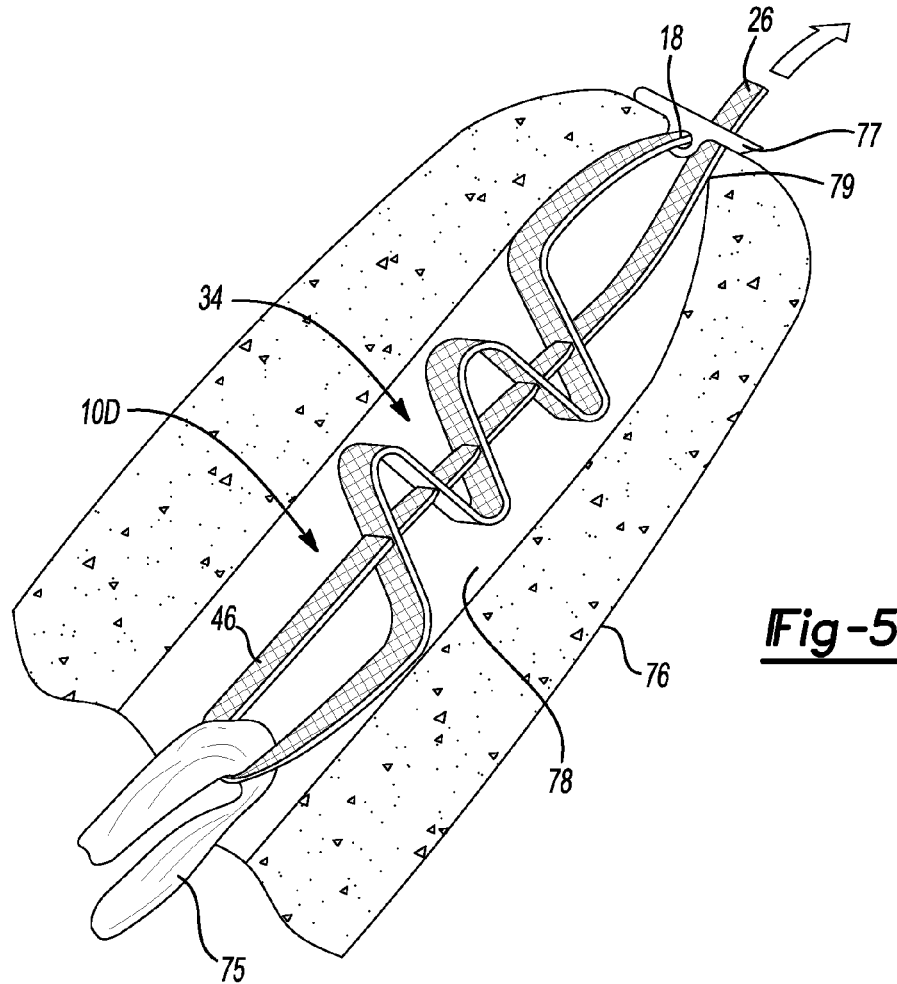
FIG. 5B is a view of an exemplary application of the self-locking adjustable loop construction of FIG. 5 depicting securing soft tissue to bone according to the present teachings.

With additional reference to FIG. 5B, an application of the adjustable loop construction 10D of FIG. 5A will now be discussed in connection with securing soft tissue 75 to a bone 76, such as a femur. In this exemplary application, soft tissue 75 can be looped around loop 46 of construction 10D and secured at its free or opposite ends (not shown). The first end 18 of construction 10D can be coupled to a fixation member such as the toggle anchor 77 illustrated. First end 18 can be passed into a bone tunnel 78 and secured relative to an end 79 of tunnel 78 opposite an end facilitating entrance of soft tissue 75 into tunnel 78, as shown in FIG. 5B. Second end 26 can also be passed through tunnel end 79 and tensioned to draw soft tissue 75 into tunnel 78 thereby tensioning and securing soft tissue 75 to bone 76.

By applying tension to second end 26, the size of loop 46 can be reduced to a desired size resulting in soft tissue 75 being tensioned, which results in a tensile force being applied to construction 10D by soft tissue 75 relative to secured end 18 and tensioned end 26. The tensile force can cause the suture 14 to constrict and thereby reduce in diameter due to the axial tensile load being applied. In addition, the legs 38 can squeeze or constrict around the portions of second portion 30 passing therethrough, which creates a mechanical interface between the interior portions or apertures of the legs 38 that are constricting around the portions of the second portion 30 passing therethrough. As a result, under tension, the mechanical interface along with the transverse force applied by each leg 38 can efficiently lock the second portion 30 to the accordion configuration 34 at a desired size of loop 46 and secure soft tissue 75 to bone 76.

Figure 6:
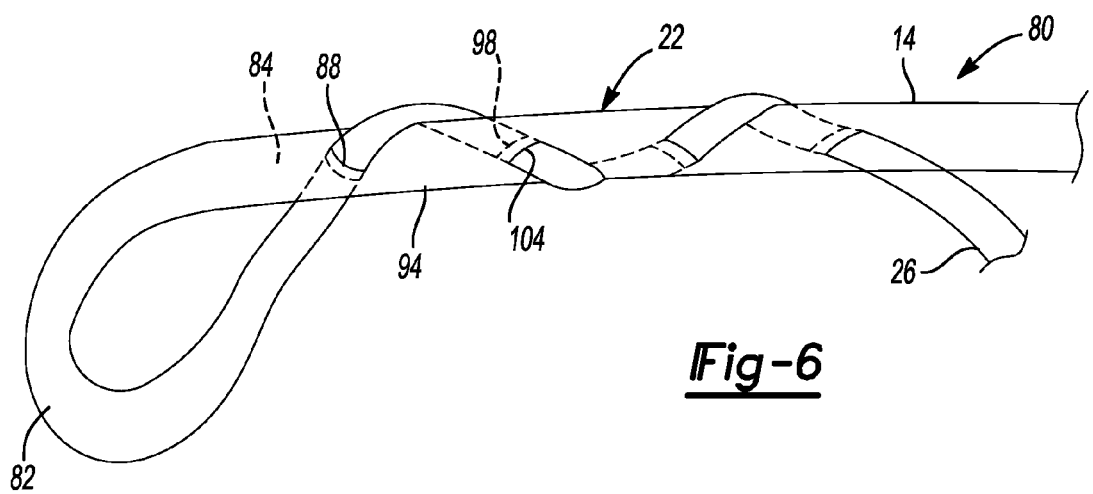
FIG. 6 is a view of an exemplary alternative self-locking adjustable loop construction according to the present teachings.

With additional reference to FIG. 6, another alternative self-locking adjustable loop construction 80 is provided. Adjustable loop construction 80 can form an adjustable loop 82 by initially passing or piercing second end 26 through first portion 22 of suture 14 on a first side 84 thereof. Second end 26 can then exit first portion 22 at point or aperture 88 on a second side 94 thereof opposite the first side 84, noting that with respect to the view shown in FIG. 6, the first side 84 is not visible but is directly behind the visible second side 94. Second end 26 can then be wrapped partially around suture 14 to subsequently enter first portion 22 on first side 84 at a second point or aperture 98, opposite of the last exit point 88 on second side 94. The second end 26 can then exit first portion 22 at point or aperture 104 on second side 94. This pattern can continue for a desired number of times, with each successive partial wrap-around and pass-through of second end 26 relative to first portion 22 providing additional self-locking capability, as discussed below. It should be appreciated that the second end 26 can be partially wrapped around first portion 22 between an exit point and an entry point, such as apertures 88 and 98, by varying amounts including 180 degrees and/or 90 degrees.

Upon applying tension to first end 18 of suture 14, the size of loop 82 can be reduced to a desired size or load. At this point, tension can be applied to the first portion 22 of the suture 14 from both the loop side and the first end 18 such that the diameter of the first portion constricts or reduces in size. This reduction in diameter applies a constricting or squeezing force on the portions of suture 14 passing through the first portion 22 thereby locking these portions relative to the first portion 22 and thus the desired size of loop 82. In addition, the suture portions that are partially wrapped around the outside of first portion 22 can provide additional frictional engagement and resistance to movement once tensioned. In this regard, having the suture portions wrap around first portion 22 by an amount of 180 degrees, as shown in FIG. 6, provides for more surface area for more frictional engagement during tensioning.

It should be appreciated that while suture 14 is shown in FIG. 6 as having a generally round or non-flat shape in cross-section, other shapes can be used to form the self-locking adjustable loop construction 80, such as the flat ribbon or braid structure 74. While adjustable loop construction 80 has been shown with one loop 82, it should also be appreciated that construction 80 could include a double loop bow tie configuration that can be formed by passing first end 18 back through first portion 22 after the second end 26 has been passed through as described above. First end 18 can be passed back through in an opposite direction, but similar manner as second end 26.

Figure 7:
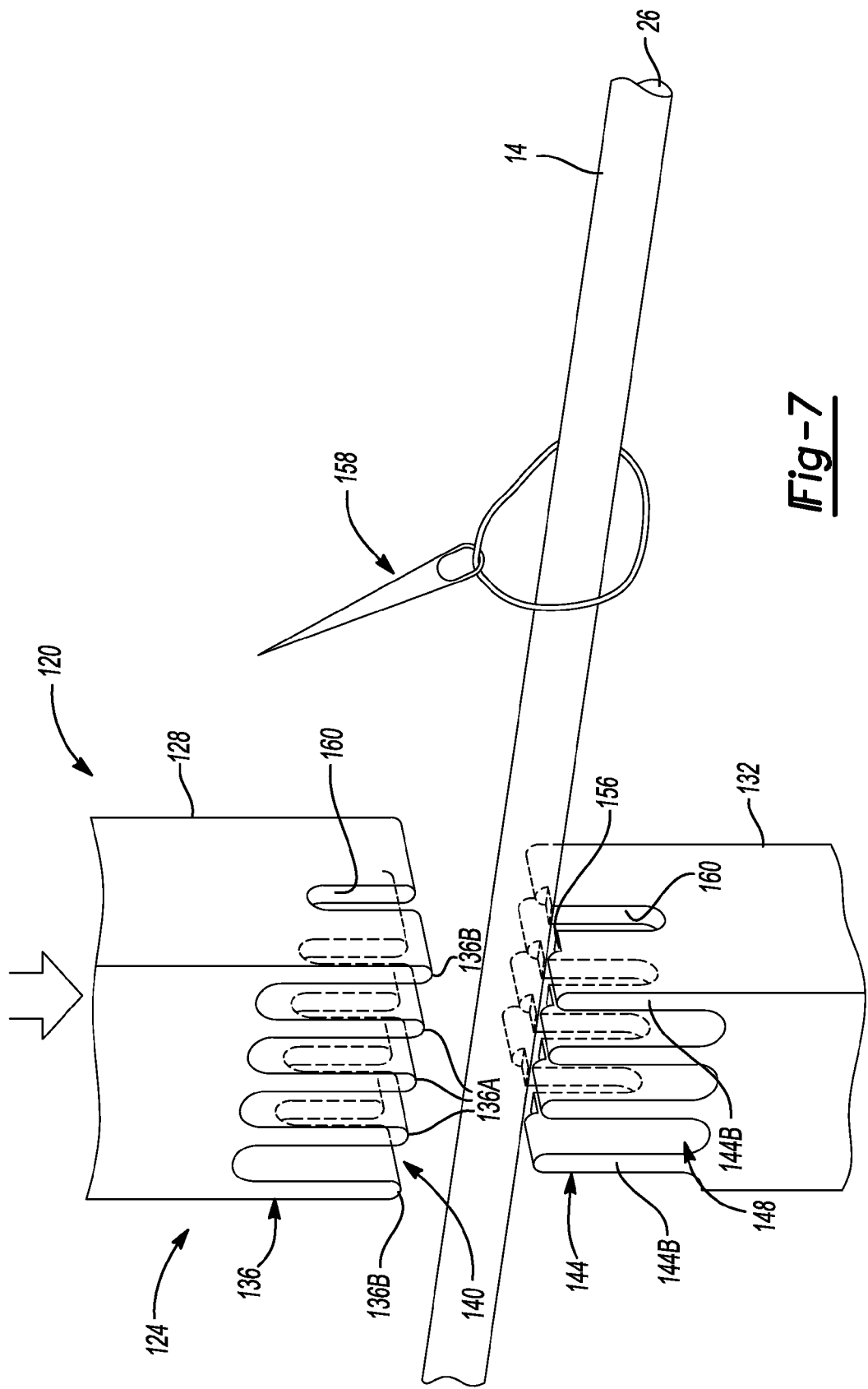
FIG. 7 is a view of an exemplary apparatus for forming a self-locking adjustable loop construction according to the present teachings.
Figure 8:
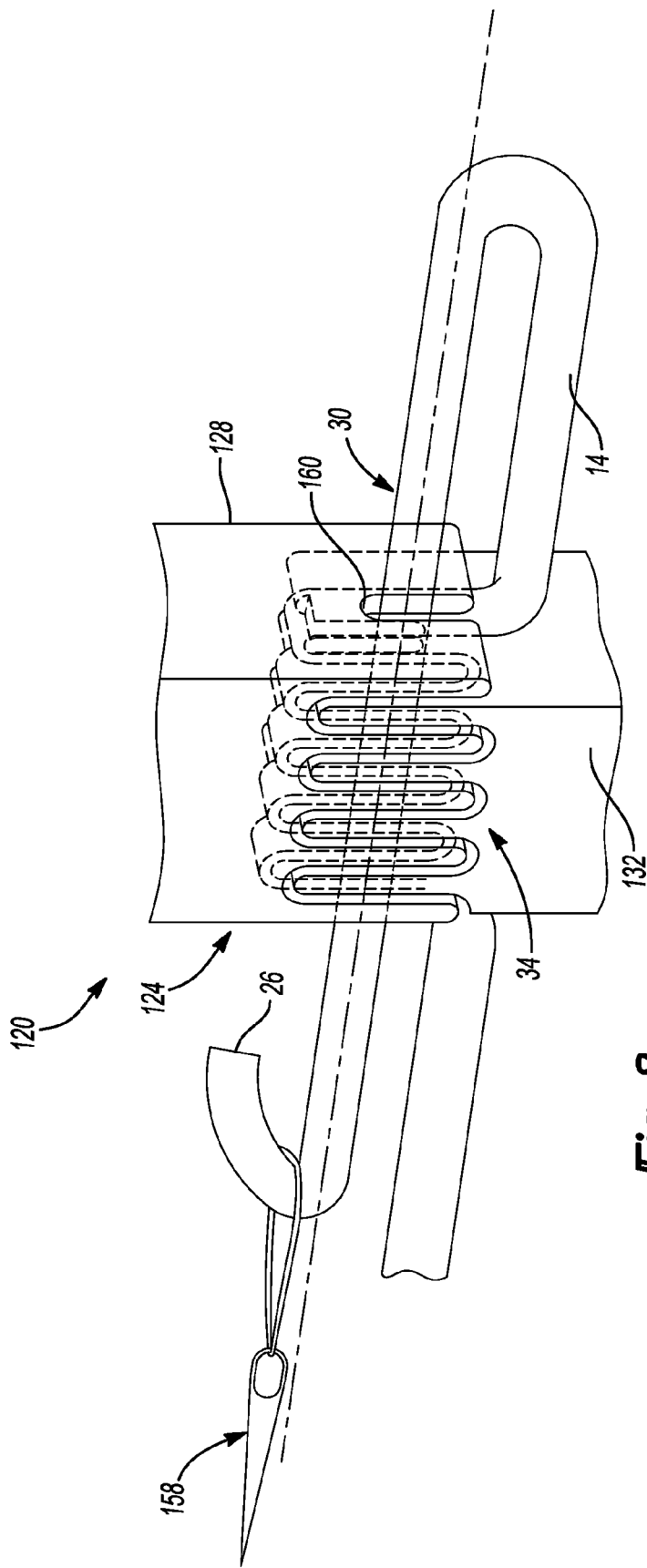
FIG. 8 is a view of the exemplary apparatus of FIG. 7 in an alternate position according to the present teachings.
Figure 9:
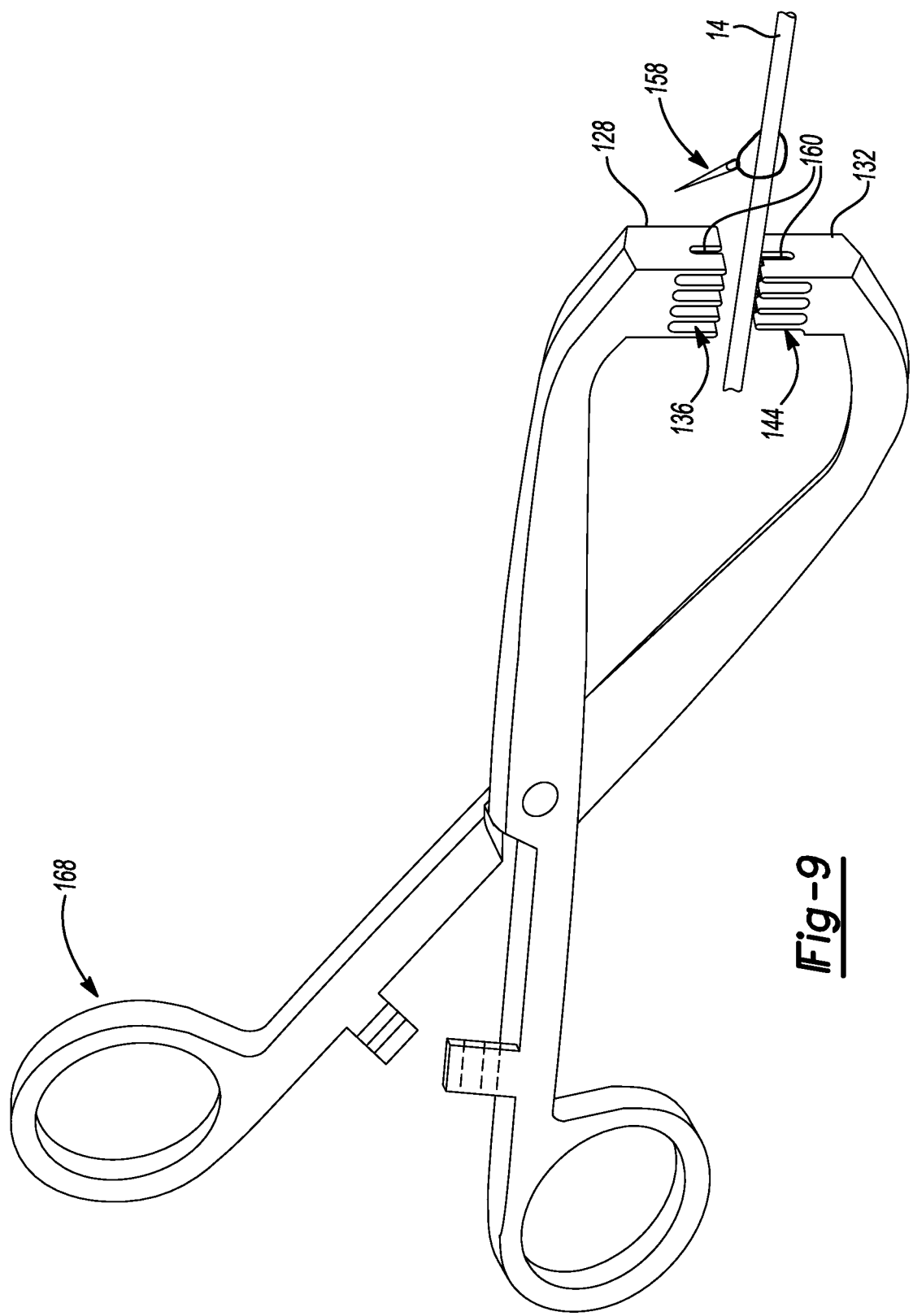
FIG. 9 is a view of the exemplary apparatus of FIG. 7 coupled to a device according to the present teachings.

With additional reference to FIGS. 7-9, an exemplary apparatus 120 that can be used for forming the self-locking adjustable loop constructions 10, 10A and 10B is shown. Apparatus 120 can include a die or similar structure 124 suitable for forming the accordion configuration 34 discussed above. Die 124 can include a first member 128 and a second member 132, as shown in FIG. 7. First member 128 can include a first plurality of fingers or projections 136 extending therefrom and spaced apart from each other by a first space or gap 140. Similarly, second member 132 can include a second plurality of projections 144 extending therefrom and spaced apart from each other by a second gap 148, as also shown in FIG. 7.

The first and second members 128, 132 can be configured to intermesh with each other such that second projections 144 are received in corresponding first gaps 140, as shown in FIG. 8. As there can be more first projections 136 than second projections 144, an interior subset 136A of the first projections 136 can be received in the corresponding spaces 148 while outer projections 136B can be received on an outer side of corresponding outer projections 144B of second projections 144, as shown in FIG. 8.

With particular reference to FIGS. 7 and 8, operation of the die 124 will be described in greater detail. A flexible member, such as suture 14 or ribbon 74, can be placed in a groove or track 156 in second member 132 so as to serve as a guide or locator for the respective suture placed therein. First member 128 can then be closed onto second member 132 such that the respective projections intermesh as described above and form the accordion pattern of the respective suture therebetween, as shown in FIG. 8 with reference to FIG. 2.

Once the members 128, 132 of die 124 are closed with a suture therebetween as described above, a needle or other suitable passing member 158 can be used to pass second end 26 through a slot 160 in each of the projections 136, 144 and pierce through legs 38 of the accordion configuration 34, as also shown in FIG. 8. Piercing the second end through legs 38 with passing member 158 can form apertures through each of the respective legs 38, as discussed herein. It should be appreciated that various different numbers of projections 136, 144 can be used, including more or less projections 136, 144 than shown in FIGS. 7-8 to arrive at an accordion configuration 34 with a desired number of legs 38. It should also be appreciated that while die 124 has been described as having groove 156 associated with second member 132 as well as second member 132 having less projections than first member 128, die 124 could be configured in an opposite manner where first member 128 include the groove as well as more fingers than second member 132.

With continuing reference to FIGS. 7-8 and additional reference to FIG. 9, die 124 can be in the form of a stand-alone configuration (as discussed above) for use on a base structure, such as an operating room table for intraoperatively forming the self-locking adjustable loop constructions 10, 10A and 10B discussed above. Alternatively, first and second members 128, 132 can be formed on or attached to respective ends of a movement device, such as forceps 168 shown in FIG. 9. In this manner a surgeon, clinician or the like can easily manipulate the first and second members 128, 132 along with a respective suture to form the accordion configuration 34 and desired self-locking adjustable loop construction 10, 10A and 10B intraoperatively.

Figure 10:
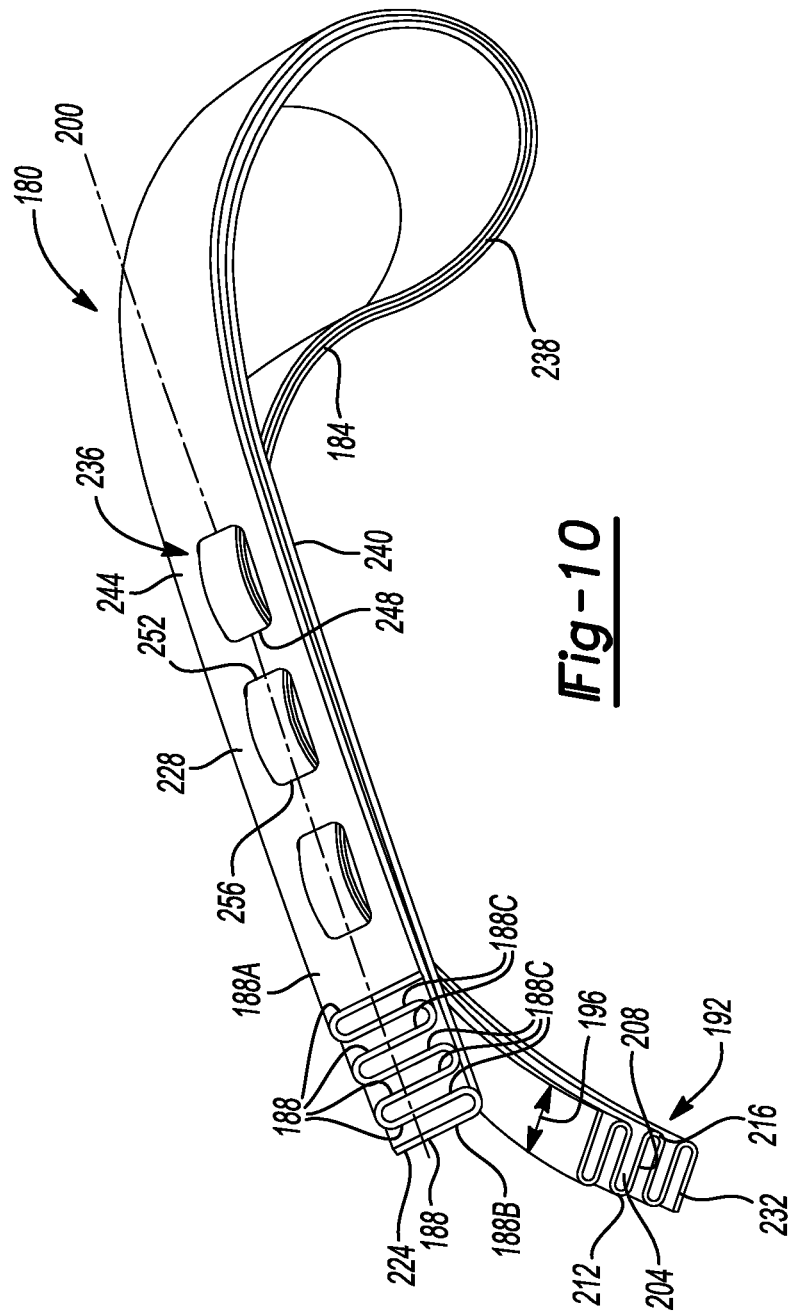
FIG. 10 is a view of an exemplary alternative self-locking adjustable loop construction according to the present teachings.

Turning now to FIGS. 10-14, an alternative self-locking adjustable loop construction 180 is shown, as well as an exemplary apparatus that can be used for forming construction 180. With particular reference to FIG. 10, adjustable loop construction 180 can be formed from a suture or graft 184. Graft 184 can be formed to include a plurality of layers 188 connected to each other in an accordion or pleated configuration 192 such that each of the layers 188 are parallel to or substantially parallel to each other in a compressed or flattened state of graft 184. In this regard, the discussion of adjustable loop construction 180 will continue with reference to using a graft 184 (shown in an exemplary non-pleated form in FIG. 13), while it should be understood that construction 180 could also be formed in the same manner from a suitable suture material. Graft 184 can be any graft suitable for forming the pleated configuration 192 discussed above, including a fascia late allograft or autograft.

In the exemplary configuration shown in FIG. 10, each layer 188 can have the same width 196 in a direction perpendicular to a longitudinal length of graft 184, as shown with reference to longitudinal axis 200. The plurality of layers 188 can include a top layer 188A, a lower or bottom layer 188B and one or more intermediate layers 188C therebetween. Each intermediate layer 188C can include an upper surface 204 and an opposite lower surface 208 and can be connected to a layer adjacent the upper surface 204 on a first side 212 and connected to a layer adjacent the lower surface 208 on a second opposite side 216, as shown in FIG. 10. In this manner, it should be appreciated that graft 184 is continuous from top layer 188A through intervening connected layers 188B to bottom layer 188C. Graft 184 can include a varying number of intermediate layers 188C as may be required to, for example, achieve a certain desired strength of graft 184.

Graft 184 can include a first end 224, a first portion 228 adjacent first end 224, and a second opposite end 232, as shown in FIG. 10. Adjustable loop construction 180 can be formed by passing second end 232 through first portion 228 in an alternating fashion forming a weave-like pattern 236 and a self-locking adjustable loop 238, as shown in FIG. 10. More particularly, second end 232 can be initially passed through each layer 188 of the pleated configuration 192 from a first side 240 of the first portion 228 and then be passed through each layer 188 of pleated configuration 192 from a second opposite side 244 of first portion 228 at a second point 248 axially spaced apart from the initial pass through point, as shown in FIG. 10.

Second end 232 can then be passed though first portion 228 at a third point 252 starting from the first side 240 and exiting on the second side 244, where the third point 252 is axially spaced apart from the second point in a direction away from the initial pass through point. The pattern 236 can continue with second end 232 being passed through first portion 228 at a fourth point 256 starting from the second side 244 and exiting on the first side 240, where the fourth point 256 is axially spaced apart from the third point 252 also in a direction away from the initial pass through point, as shown in FIG. 10. Second end 232 can be passed through first portion 228 at each of the first through fourth points in a direction other than parallel to longitudinal axis 200 of first portion 228, including a direction perpendicular or substantially perpendicular thereto.

In operation, the loop 238 can be adjusted by placing tension on second end 232 to move second end relative to first portion 228 thereby reducing the size of loop 238 to a desired size or load. At this point, tension can be applied on first portion 228 by loop 238 thereby causing a restriction in width 196. The restriction in width 196 can apply a squeezing or constricting force against the portions of graft 184 weaving through first portion 228 in a manner similar to discussed above. The constricting force combined with the alternative weave pattern can lock the loop at the desired size or load under tension relative to first portion 228.

Figure 11:
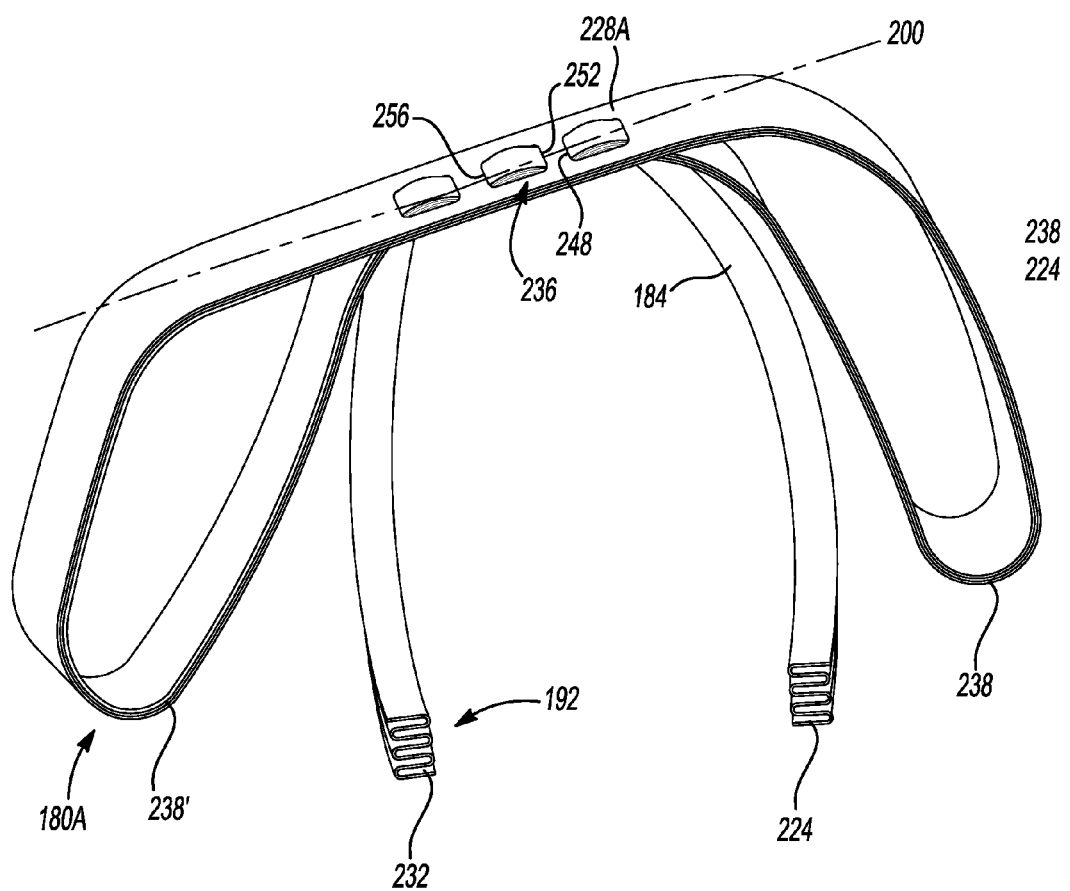
FIG. 11 is a view of an alternative construction of the adjustable loop construction of FIG. 10 having two loops according to the present teachings.

With additional reference to FIG. 11, an alternative self-locking adjustable loop construction 180A is shown that can include an additional adjustable loop 238' thereby forming a bow tie configuration. Adjustable loop construction 180A can be formed and can function in a similar manner as adjustable loop construction 180, except two loops 238, 238' are provided and available for securing to bone, soft tissue, or other devices. More specifically, adjustable loop construction 180A can be formed by taking first end 224 and passing it back through the portion 228A of the graft 184 in this configuration having the weave pattern 236 described above. First end 224 can be passed through portion 228A in an opposite axial or longitudinal direction as second end 232 using the same pass through points 248-256 to mimic the weave pattern 236, where the portion of graft passed back though by the first end 224 can rest on top of weave pattern 236 thereby forming a complimentary weave pattern, as shown in FIG. 11.

In operation, tension can be applied to both first and second ends 224, 232 until the corresponding loops 238, 238' are reduced to the desired size and/or load. At this point, the tension applied by the loops and the respective ends can cause the width reduction and constricting forces discussed above that, along with the weave patterns, can thereby lock the loops 238, 238' relative to the central weave configurations. In addition, the portions of graft 184 associated with the first and second ends that form the weave patterns in this configuration can be contiguous to each other thereby causing additional friction and resistance to relative movement under tensile load.

Figure 12A:
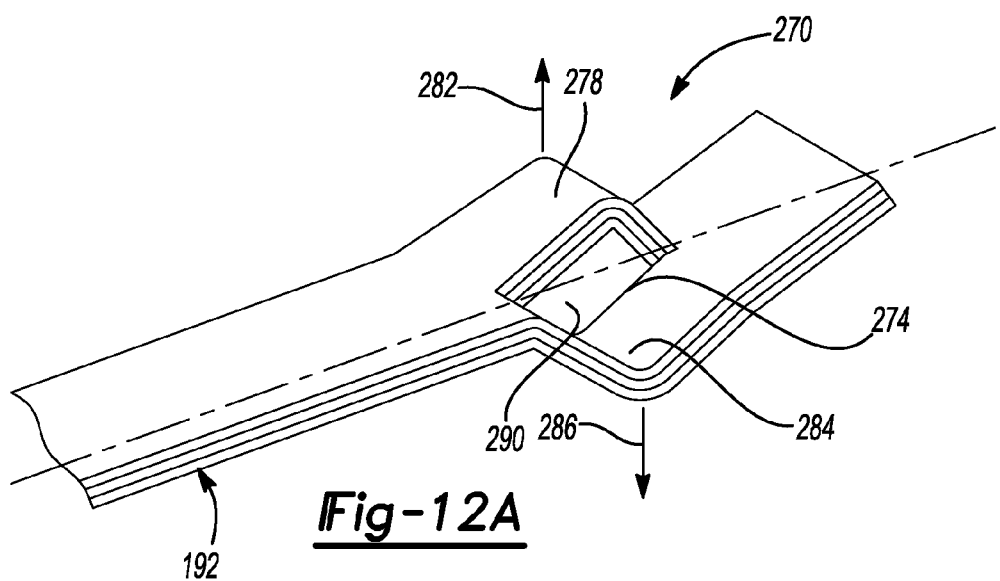
FIGS. 12A and 12B are views of an exemplary retention feature for the self-locking adjustable loop configurations according to the present teachings.
Figure 12B:
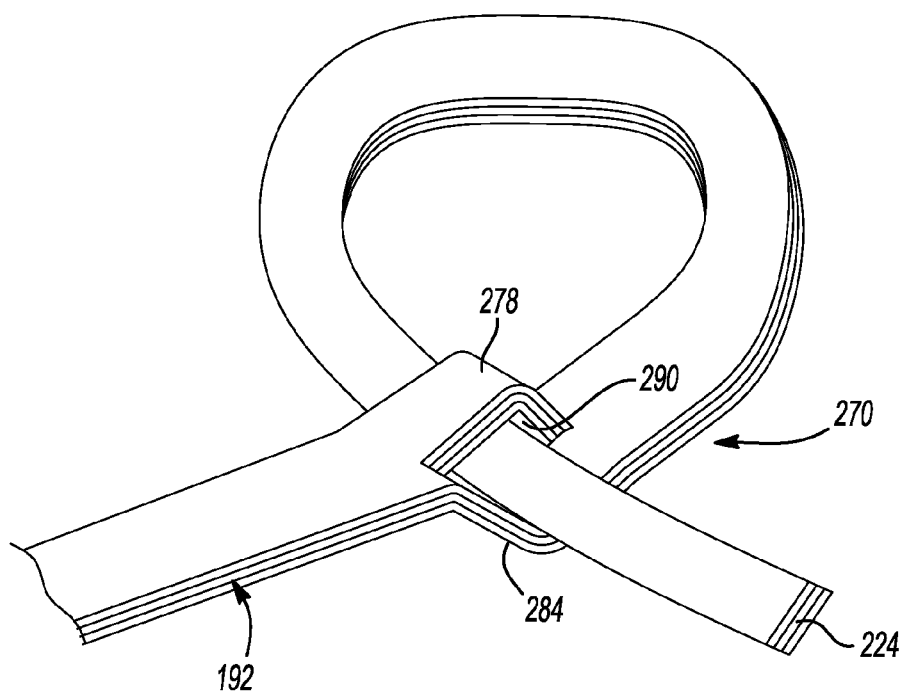

With additional reference to FIGS. 12A-12B, an arrangement 270 for retaining or securing first end 224 of suture or graft 184 of adjustable loop construction 180 is provided. The arrangement 270 can include an aperture or slot 274 through each layer of the pleated configuration 192, as shown in FIG. 12A. The slot 274 can be formed parallel to a longitudinal axis of the graft 184 as shown, or in another orientation such as perpendicular thereto. A portion of the graft 184 adjacent a first side 278 of slot 274 can be moved away from slot 274 in a first direction 282 and a portion of the graft 184 on a second opposite side 284 of the slot 274 can be moved away in a second direction 286 opposite the first direction 282 thereby forming an opening 290. First end 224 can then be routed through opening 290 where the pleated configuration 192 can slightly expand against the opening and thereby assist in securing and retaining first end 224 in the pleated configuration 192, as shown in FIG. 12B. Passing first end 224 through opening 290 as discussed above can prevent the pleated configuration 192 at first end 224 from unfolding or separating.

It should be appreciated that pleated configuration 192 of suture or graft 184 can also be used to form the self-locking adjustable loop constructions 10, 10A, 10B and 80 discussed above with reference to FIGS. 2-6.

Figure 14B:
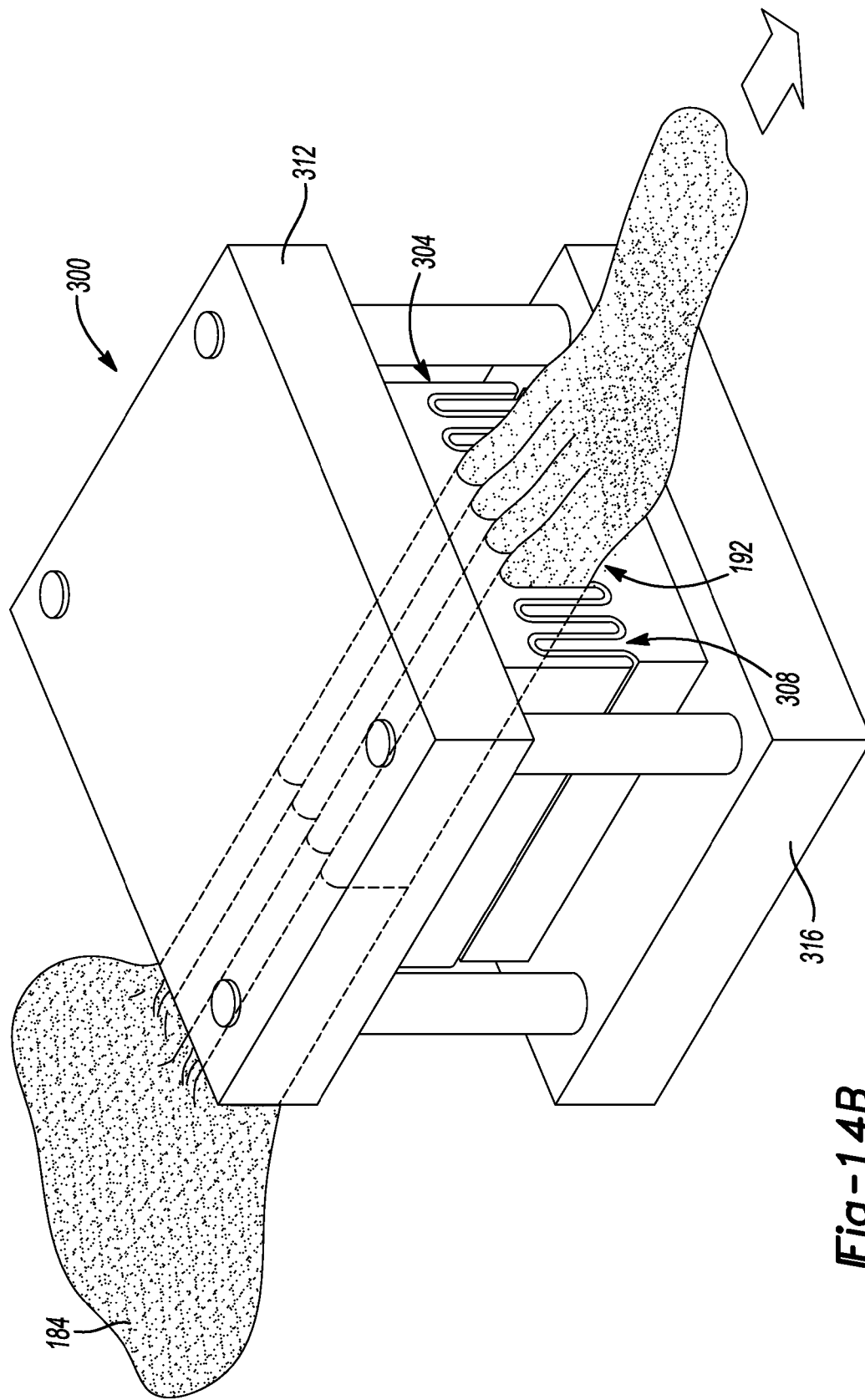

Turning now to FIGS. 13-14B, a forming device, such as a die 300, is provided and can be used for forming graft 184 in the pleated configuration 192 discussed above with reference to FIGS. 10 and 11. Graft 184, in the non-pleated form shown generally in FIG. 13, can be placed in die 300 and translated axially relative to the die to form the pleated configuration 192. Die 300 can include a similar construction to die 124 where a plurality of projections 304 and 308 protrude from respective first and second members 312 and 316, as shown in FIG. 14A. Upon closing the die 300, the projections 304, 308 can intermesh to shape the graft 184 placed therebetween into the pleated configuration 192, as shown in FIG. 14B.

The projections 304, 308 can be configured such that when they intermesh, there is enough clearance between the projections such that the graft 184 can be translated axially relative to die 300. Translation of graft 184 relative to die 300 can form the pleated configuration 192 along a longitudinal length of the graft 184 that is longer than a corresponding length of the die 300, as shown in FIG. 14B. In this manner, a relatively small and portable die 300 is provided that can be used intraoperatively to form a graft into the pleated configuration 192 for use in the self-locking adjustable loop constructions 180, 180A discussed above, as well as in adjustable loop constructions 10, 10A and 10B. The members 312, 316 of die 300 can also be coupled to or integrally formed with a movement device, such as forceps 168 to aid in opening and closing the die 300, as discussed above with reference to die 124 and FIG. 9.

The adjustable loop constructions described herein can be used in various surgical procedures to affect closure, secure a graft to soft tissue or bone, or in a ligament repair procedure, such as an ACL repair procedure. In an exemplary ligament repair procedure, for example, the single or double loop constructions disclosed herein can be used to secure a natural or artificial ACL to a fixation member, as disclosed in the above cases incorporated herein by reference. Further, the adjustable loop construction 180 formed from graft 184 can act as an ACL replacement in either the single or double loop configuration. Each of the adjustable loop constructions described herein can also serve to draw an ACL component up through a tibial tunnel and into a femoral tunnel, as well as adjust a tension of the ACL component.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A method of forming a self-locking adjustable loop, comprising:
   providing a flexible member having a first end, a second end and a first portion and a second portion therebetween;
   passing in a first direction the first end of the flexible member through the first portion at a first point such that the first end passes through the first portion from a first side of the flexible member to a second opposite side of the flexible member;
   passing in the first direction the first end of the flexible member through the first portion at a second point spaced apart from the first point such that the first end passes through the first portion from the second side of the flexible member to the first opposite side of the flexible member so as to place the first end outside of the first portion, wherein the first end is passed through the first and second points in the first direction other than parallel to a longitudinal axis of the first portion to form a first adjustable loop; and
   passing the second end of the flexible member through the second portion spaced apart from the first portion in a second direction opposite the first direction the first end passes through the first portion to form a second adjustable loop.

2. The method according to claim 1, further comprising:
   forming the first portion into an accordion configuration having a plurality of leg portions connected to each other;
   wherein passing in the first direction the first end of the flexible member through the first portion at a first point includes passing the first end though a first leg portion of the plurality of leg portions from the first side to the second side of the first portion in a direction other than parallel to a longitudinal axis of the first leg portion; and
   wherein passing in the first direction the first end through the first portion at a second point includes passing the first end through a second leg portion adjacent the first leg portion such that the first end passes through the second leg portion from the second side to the first side of the first portion in a direction other than parallel to a longitudinal axis of the second leg portion so as to place the first end outside of the accordion configuration.

3. The method according to claim 2, wherein forming the first portion into an accordion configuration includes forming the first portion into an accordion configuration having at least six leg portions.

4. The method according to claim 2, further comprising passing the first end through the first and second leg portions in the first direction substantially perpendicular to the respective, longitudinal axes of the first and second leg portions.

5. The method of claim 2, further comprising forming the first portion into the accordion configuration proximate the second end of the flexible member.

6. The method according to claim 2, further comprising passing the second end of the flexible member through the first and second leg portions of the second portion in the second direction opposite the first direction the first end was passed through the first and second leg portions of the first portion to form the two adjustable loops.

7. The method according to claim 6, wherein passing the second end of the flexible member through the first and second leg portions of the second portion includes passing the first end through the first leg portion from a first side to a second side of the second portion and then passing the second end through the second leg portion from the second side to the second side of the second portion.

8. The method according to claim 2, further comprising:
   providing a portable flexible member forming device having first and second members each having a plurality of projections extending therefrom that are configured to intermesh with each other when the forming device is moved from an open position to a closed position;
   positioning the first portion of the flexible member between the plurality of projections of the respective first and second members in the open position such that a longitudinal length of the flexible member is substantially perpendicular to a longitudinal length of each of the plurality of projections of the first and second portions;
   forming the first portion into the accordion configuration intraoperatively by moving the first and second members to the closed position such the respective pluralities of projections intermesh with each other while the flexible member is positioned therebetween; and
   passing the first end of the flexible member through an access port of the forming device in the closed position such that the first end passes in the first direction through the first and second leg portions.

9. The method according to claim 1, wherein providing a flexible member includes providing a suture having a solid construction formed with a braided structure, a ribbon structure, or a monofilament structure, or combinations thereof.

10. The method according to claim 1, wherein providing a flexible member includes providing braided ribbon construction having a rectangular shape in cross-section.

11. The method according to claim 1, further comprising forming the flexible member into a pleated configuration having a plurality of interconnected layers extending along an entire length of the flexible member, the plurality of interconnected layers configured to be substantially parallel to each other in a compressed state of the flexible member.

12. The method according to claim 1, wherein passing the first end of the flexible member through the first portion at the first point includes passing the first end of the flexible member through the first portion at the first point such that the first end passes through the first portion from the first side of the flexible member to the second opposite side of the flexible member in the first direction other than parallel to the longitudinal axis of the first portion; and wherein passing the first end through the first portion at the second point includes passing the first end through the first portion at the second point spaced apart from the first point such that the first end passes through the first portion from the second side of the flexible member to the first side of the flexible member in the first direction other than parallel to the longitudinal axis of the first portion.

13. The method according to claim 1, further comprising passing in the second opposite direction the second end of the flexible member through first and second leg portions of the second portion where the second end is passed through the first leg portion from a first side to a second side of the second portion and passed through the second leg portion from the second side to the first side of the second portion.

14. A method of forming a self-locking adjustable loop, comprising:
providing a flexible member having a first end, a second end, and a first portion and a second portion therebetween;
passing in a first direction the first end of the flexible member through the first portion at a first point such that the first end passes through the first portion from a first side of the flexible member to a second opposite side of the flexible member in the first direction other than parallel to a longitudinal axis of the first portion;
passing in the first direction the first end through the first portion at a second point such that the first end passes through the first portion from the second side of the flexible member to the first side of the flexible member in the first direction other than parallel to the longitudinal axis of the first portion so as to place the first end outside of the first portion, the second point being spaced apart longitudinally from the first point; and
passing the second end of the flexible member through the second portion spaced apart from the first portion in a second direction opposite the first direction the first end passes through the first portion to form two adjustable loops.

15. The method according to claim 14, further comprising:
passing in the first direction the first end through the first portion at a third point from the first side of the flexible member to the second side of the flexible member, and passing in the first direction the first end through the first portion at a fourth point from the second side of the flexible member to the first side of the flexible member;
wherein the third and fourth points are spaced apart from each other and the first and second points.

16. The method according to claim 15, wherein passing the first end through the first portion at the first, second, third and fourth points includes passing the first end through the first portion at the first, second, third and fourth points in the first direction substantially perpendicular to the longitudinal axis of the first portion.

17. A method of forming a self-locking adjustable loop comprising:
providing a flexible member having a first end, a second end, a first portion, and a spaced apart second portion between the first end and the second end;
passing in a first direction the first end of the flexible member through the first portion at a first point such that the first end passes through the first portion from a first side to a second opposite side of the first portion;
passing in the first direction the first end through the first portion at a second point spaced apart from the first point such that the first end passes through the first portion from the second side to the first side of the first portion to form a first adjustable loop;
passing in a second opposite direction the second end of the flexible member through the second portion at a third point such that the second end passes through the second portion from a first side to a second opposite side of the second portion; and
passing in the second opposite direction the second end through the second portion at a fourth point spaced apart from the third point such that the second end passes through the second portion from the second side to the first side of the second portion to form a second adjustable loop.

18. The method according to claim 17, wherein passing the first end of the flexible member through the first portion at the first point includes passing the first end of the flexible member through the first portion at the first point such that the first end passes through the first portion from the first side to the second opposite side in the first direction other than parallel to the longitudinal axis of the first portion; and
wherein passing the first end through the first portion at the second point includes passing the first end through the first portion at the second point spaced apart from the first point such that the first end passes through the first portion from the second side to the first side in the first direction other than parallel to the longitudinal axis of the first portion.

* * * * *